US011655450B2

(12) United States Patent
Cho et al.

(10) Patent No.: US 11,655,450 B2
(45) Date of Patent: May 23, 2023

(54) METHOD FOR INDUCING DIFFERENTIATION OF STEM CELL INTO DOPAMINERGIC NEURAL PRECURSOR CELL

(71) Applicant: S-BIOMEDICS, Seoul (KR)

(72) Inventors: Myung Soo Cho, Gyeonggi-do (KR); Jang Hyeon Eom, Gyeonggi-do (KR); Seung Taek Nam, Seoul (KR)

(73) Assignee: S-BIOMEDICS, Seoul (KR)

( * ) Notice: Subject to any disclaimer, the term of this patent is extended or adjusted under 35 U.S.C. 154(b) by 357 days.

(21) Appl. No.: 16/652,563

(22) PCT Filed: Mar. 25, 2020

(86) PCT No.: PCT/KR2020/004065
§ 371 (c)(1),
(2) Date: Mar. 31, 2020

(87) PCT Pub. No.: WO2021/060637
PCT Pub. Date: Apr. 1, 2021

(65) Prior Publication Data
US 2021/0238547 A1 Aug. 5, 2021

(30) Foreign Application Priority Data

Sep. 25, 2019 (KR) .......... 10-2019-0118370
Mar. 5, 2020 (KR) .......... 10-2020-0027801

(51) Int. Cl.
*C12N 5/0797* (2010.01)

(52) U.S. Cl.
CPC ...... *C12N 5/0623* (2013.01); *C12N 2501/155* (2013.01); *C12N 2501/16* (2013.01);
(Continued)

(58) Field of Classification Search
None
See application file for complete search history.

(56) References Cited

U.S. PATENT DOCUMENTS 8,492,149 B2   7/2013   Cho et al.
8,551,783 B2   10/2013  Kim et al.
(Continued)

FOREIGN PATENT DOCUMENTS

JP   2012-501194 A   1/2012
JP   2012-210805 A   11/2012
(Continued)

OTHER PUBLICATIONS

Schulz, Thomas C; et al; "Directed neuronal differentiation of human embryonic stem cells" BMC Neuroscience, 4, 1-13, 2003 (Year: 2003).*

(Continued)

*Primary Examiner* — David W Berke-Schlessel
(74) *Attorney, Agent, or Firm* — Harness, Dickey & Pierce, P.L.C.

(57) ABSTRACT

Disclosed herein are a method for inducing differentiation of stem cells into dopaminergic neural precursor cells and a method for mass production of dopaminergic neural precursor cells. Having ability to effectively differentiate stem cells into neural precursor cells, the methods can find advantageous applications in research and development and commercialization associated therewith.

14 Claims, 26 Drawing Sheets

Specification includes a Sequence Listing.

(52) U.S. Cl.
CPC .... *C12N 2501/41* (2013.01); *C12N 2501/727* (2013.01); *C12N 2506/45* (2013.01)

(56) References Cited

U.S. PATENT DOCUMENTS

| | | |
|---|---|---|
| 2010/0317103 A1 | 12/2010 | Cho et al. |
| 2011/0217774 A1 | 9/2011 | Kim et al. |
| 2011/0229441 A1 | 9/2011 | Benchoua et al. |
| 2014/0199274 A1 | 7/2014 | Kim et al. |
| 2016/0160177 A1 | 6/2016 | Benchoua et al. |
| 2016/0215260 A1 | 7/2016 | Takahashi et al. |
| 2018/0265843 A1 | 9/2018 | Benchoua et al. |
| 2019/0112575 A1 | 4/2019 | Takahashi et al. |
| 2019/0330590 A1 | 10/2019 | Cho et al. |

FOREIGN PATENT DOCUMENTS

| | | |
|---|---|---|
| KR | 10-2007-0117440 A | 12/2007 |
| KR | 10-2011-0023129 A | 3/2011 |
| KR | 10-2011-0050310 A | 5/2011 |
| KR | 10-2016-0053936 A | 5/2016 |
| KR | 101783977 B1 | 10/2017 |
| KR | 10-2018-0135918 A | 12/2018 |
| WO | WO-2017/183736 A1 | 10/2017 |

OTHER PUBLICATIONS

Llames, Sara; et al; "Feeder Layer Cell Actions and Applications" Tissue Engineering: Part B, 21, 345-353, 2015 (Year: 2015).*
Vemuri, Mohan C; "Neural Differentiation of Pluripotent Stem Cells" Neural Stem Cell Assays, 1-7, 2014 (Year: 2014).*
Notice of Allowance from corresponding Korean Patent Application No. 10-2020-0027801, dated Jan. 28, 2022.
Office Action from corresponding Japanese Patent Application No. 2020-518613, dated Jan. 25, 2022.
International Search Report from corresponding PCT/KR2020/004065, dated Jul. 9, 2020.
Written Opinion from corresponding PCT/KR2020/004065, dated Jul. 9, 2020.
Office Action from corresponding Russian Patent Application No. 2020112673, dated Nov. 3, 2022.
Sujoy K Dhara et al. Neural Differentiation of Human Embryonic Stem Cells, Journal of Cellular Biochemistry 105:633-640 (2008).
S.V. Anisimov. Cell Therapy for Parkinson's Disease II. Stem Cell-Based Applications, Successes gerontol. 2009. T. 22.No. 1. S. 150-166.

* cited by examiner

Step of generating neural rosette
(Treatment with SAG and CHIR99021 from difference day 6)

Step of generating neural rosette
(Treatment with SAG and CHIR99021 from difference day 10)

Treatment with SAG and CHIR99021 ceased on differentiation day 20

Treatment with SAG and CHIR99021 ceased on differentiation day 35

Problem in attaching dopaminergic precursor cells with CELLstart

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: En1-F

<400> SEQUENCE: 1
cgtggcttac tccccattta                                              20

<210> SEQ ID NO 2
<211> LENGTH: 20
<212> TYPE: DNA
<213> ORGANISM: Artificial Sequence
<220> FEATURE:
<223> OTHER INFORMATION: En1-R

<400> SEQUENCE: 2
tctcgctgtc tctccctctc                                              20

<210> SEQ ID NO 3
<211> LENGTH: 20
<212> TYPE: DNA
<213> ORGANISM: Artificial Sequence
<220> FEATURE:
<223> OTHER INFORMATION: GAPDH-F

<400> SEQUENCE: 3
caatgacccc ttcattgacc                                              20

<210> SEQ ID NO 4
<211> LENGTH: 20
<212> TYPE: DNA
<213> ORGANISM: Artificial Sequence
<220> FEATURE:
<223> OTHER INFORMATION: GAPDH-R

<400> SEQUENCE: 4
ttgattttgg agggatctcg                                              20
```

METHOD FOR INDUCING DIFFERENTIATION OF STEM CELL INTO DOPAMINERGIC NEURAL PRECURSOR CELL

CROSS-REFERENCE TO RELATED APPLICATIONS

This application is a national phase application of PCT Application No. PCT/KR2020/004065, filed on Mar. 25, 2020, which claims the benefit and priority to Korean Patent Application No. KR 10-2020-0027801, filed on Mar. 5, 2020 and Korean Patent Application No. KR 10-2019-0118370, filed on Sep. 25, 2019. The entire disclosures of the applications identified in this paragraph are incorporated herein by references.

FIELD

The present invention relates to a method for inducing differentiation of stem cells into midbrain-specific dopaminergic neural precursor cells and for mass production of stem cell-derived midbrain-specific dopaminergic neural precursor cells.

BACKGROUND

The present invention was supported by a grant (project number HI18C0096) from the Ministry of Health and Welfare, Korea. The project is conducted in the project name "Function- and efficacy-based development of pluripotent stem cell-derived cl therapy product for Parkinson's disease" as the research named "Development of frontier medical technique" by the managing company S. Biomedics Co. Ltd. under the supervision of the Korea health Industry Development Institute during Apr. 30, 2018 to Dec. 31, 2022.

This patent application claims priority to and the benefit of Korean Patent Application No. 10-2019-0118370, filed Sep. 25, 2019, the entire contents of which are incorporated herein by reference.

DESCRIPTION OF THE PRIOR ART

Stem cells refer to cells remaining in a pre-differentiation phase and undergo differentiation into specific cells upon exposure to specific differentiation stimuli (environments). Unlike completely differentiated cells that do not further differentiate, stem cells can also show the proliferation (expansion) characteristic of dividing in self-renewal to produce more of the same type of the stem cells. In addition, stem cells, which differentiate into specific cells in response to differentiation stimuli, are characterized by the differentiation plasticity that cell types to which stem cells are differentiated depend on environments or stimuli to which the stem cells are exposed.

Nowadays, extensive attention is paid to stem cells for use as cell therapy products. Much research has also been conducted into the use of stem cells as cell therapy products for various neurological diseases caused by neuronal injury. Among other diseases, cranial nerve diseases are considered to be the most suitable target for cell transplantation therapy because tissues in the brain nervous system exhibits almost no immune rejection responses, unlike the other tissues and thus are expected to allow the long-term survival of cells transplanted from the outside.

Meanwhile, a technique is required for effectively differentiating stem cells into specific cells and supplying specific cells in a desired time in order to enhance the efficacy of stem cells as cell therapy products.

However, thus far, techniques have not yet been developed for differentiating stem cells into specific cells (inter alia, dopaminergic neural cells) at such a high efficiency as to allow clinical application and for storing the cells at suitable stages.

SUMMARY

Leading to the present disclosure, intensive and thorough research into the induction of stem cells to differentiate into midbrain-specific dopaminergic neural precursor cells, conducted by the present inventors, with the aim of developing cell therapy products for cranial nerve diseases, resulted in conceiving a method capable of mass production of midbrain-specific dopaminergic neural precursor cells at so high efficiency as to allow clinical application.

It is therefore a purpose of the present disclosure to provide a method for inducing stem cells to differentiate into dopaminergic neural precursors cells.

It is another purpose of the present disclosure to provide a method for mass production of dopaminergic neural precursor cells.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION

Figure 1:
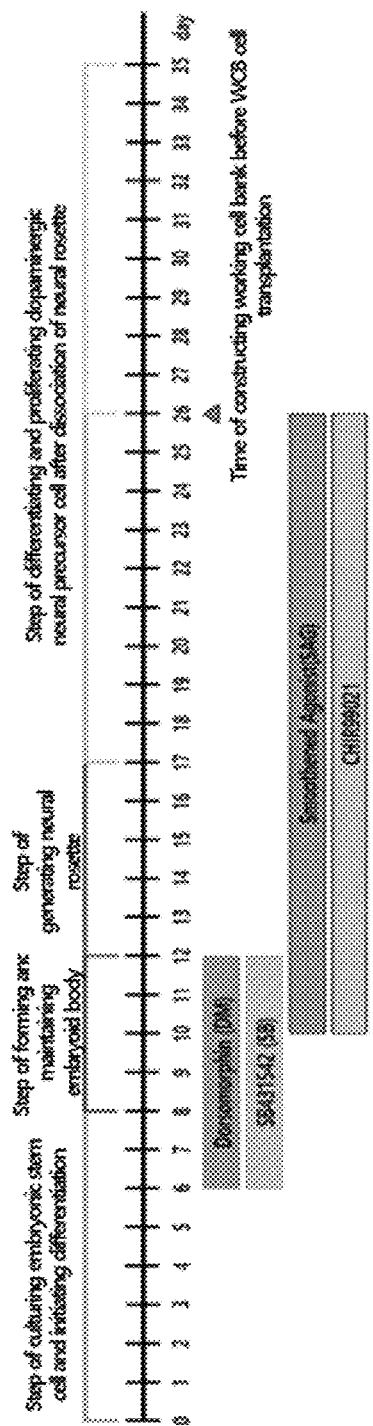
FIG. 1 is a schematic view illustrating a method for inducing differentiation into dopaminergic neural precursor cells according to an embodiment of the present disclosure.

In order to develop a cell therapy product for cranial nerve disease, the present inventors have made effects to conceive a method for inducing the differentiation of stem cells into midbrain-specific dopaminergic neural precursor cells. As a result, a method for mass production of midbrain-specific dopaminergic neural precursor cells at so high efficiency as to allow clinical application is introduced.

In addition, the present inventors have established an effective method capable of storing differentiation-induced midbrain-specific dopaminergic neural precursor cells as a working cell bank (WCB) at a suitable stage.

The present disclosure pertains to a method for inducing stem cells to differentiate into dopaminergic neural precursor cells and producing dopaminergic neural precursor cells on a mass scale.

Below, a detailed description will be given of the present disclosure.

According to an aspect thereof, the present disclosure pertains to a method for inducing stem cells to differentiate into dopaminergic neural precursor cells, the method comprising the steps of:
a) culturing stem cells in a monolayer format;
b) forming and maintaining an embryoid body;
c) generating a neural rosette; and
d) differentiating the neural rosette into dopaminergic neural precursor cells.

Hereinafter, a method for preparation of dopaminergic neural cells will be described in detail.

Step a)

This step is a process in which undifferentiated stem cells are stimulated by treatment with a BMP signaling inhibitor and an activin/nodal signaling inhibitor. In this process, the stem cells are differentiated into ectodermal cells, especially neuroectodermal cells at higher efficiency, compared to those that have not treated with such materials.

The stem cells may be embryonic stem cells, induced pluripotent stem cells (iPSCs), adult stem cells, somatic cell nuclear transfer embryonic stem cells, or stem cells generated by direct reprogramming.

This step may be conducted for 5-9 days or 8 days, but without limitations thereto.

Differentiation within the range allows embryoid bodies to be formed without collagenase. When departing from the range, the differentiation does not guarantee the generation of the desired cells, but may proceed to natural differentiation or may give problems in the next step of forming an embryoid body. Meanwhile, respective optimal periods of time may be established for individual types of the stem cells within the range because the working times of the inhibitors differ from one stem cell type to another.

In the step, a BMP signaling inhibitor and an activin/nodal signaling inhibitor may be added daily from 1-3 days before the end of the step, but without limitations thereto.

So long as it is known in the art, any BMP signaling inhibitor may be available without limitations. Examples of the BMP signaling inhibitor include dorsomorphin, Smad6, Smad7, Noggin, Chordin, Gremlin, Sog (shortgastrulation), Follistatin, DAN (differential screening=selected gene aberrant in neuroblastoma), Cerberus, Dante, and/or PRDC (Protein Related to DAN and Cerberus).

In the present disclosure, "dorsomorphin" is an inhibitor against the BMP signaling pathway, acting to inhibit BMP itself or repress the binding of BMP to a BMP receptor.

Dorsomorphin is represented by the following Chemical Formula 1:

[Chemical Formula 1]

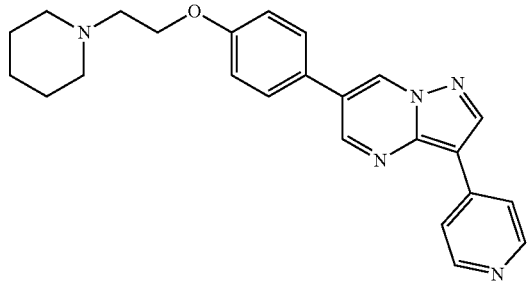

In the step, the BMP signaling inhibitor may be used at a concentration of 1.0 to 20.0 μM, at a concentration of 4.0 to 6.0 μM, or at the concentration of 5.0 μM, but without limitations thereto.

A concentration departing from the range may cause cell death. Meanwhile, respective optimal concentrations may be established for individual types of the stem cells within the range because the working concentrations of the inhibitor differ from one stem cell type to another.

Selection may be made of various activin/nodal signaling inhibitors known in the art, without limitations. Particularly, the activin/nodal signaling inhibitor useful in the present disclosure may be 4-(5-benzo[1,3]dioxol-5-yl-4-pyridin-2-yl)-imidazol-2-yl)-benzamide, Smad6, Smad7, and/or Follistatin.

In the present disclosure, "4-(5-benzo[1,3]dioxol-5-yl-4-pyridin-2-yl-1H-imidazol-2-yl)-benzimie", known as SB431542 in the art, inhibits the activin/nodal signaling pathway by suppressing activin/nodal itself or preventing activin/nodal from binding to the receptor thereof.

The 4-(5-Benzo[1,3]dioxol-5-yl-4-pyridin-2-yl-1H-imidazol-2-yl)-benzimide is represented by the following Chemical Formula 2:

[Chemical Formula 2]

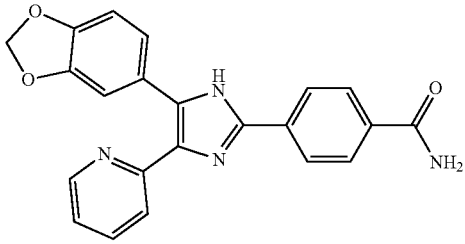

In the present disclosure, the compound represented by Chemical Formula 1 is used in combination with SB431542.

In the step, the activin/nodal signaling inhibitor may be used at a concentration of 1.0 to 50.0 µM, at a concentration of 4.0 to 6.0 µM, or at the concentration of 5.0 µM, but with no limitations thereto.

When departing from the range, a concentration of the activin/nodal signaling inhibitor may cause cell death. Meanwhile, respective optimal concentrations may be established for individual types of the stem cells within the range because the working concentrations of the inhibitor differ from one stem cml type to another.

In the step, the cells may be cultured in a TeSR2 cell culture medium. This is intended to use the cells for clinical entry and cell therapy products. In addition to the TeSR2 cell culture medium, any stem cell culture medium that allows clinical entry may be selectively employed without limitations.

Step b)

This step is a process in which an embryoid body is formed and then stimulated by treatment with a sonic hedgehog (SHH) signaling activator and a GSK-3 inhibitor while being cultured. In this process, the embryoid body is differentiated into dopaminergic neural precursor cells at higher efficiency, compared to those that have not been treated with such materials.

As used herein, the term "embryoid body" refers to a three-dimensional aggregate of pluripotent stem cells of which embryonic stem cells are representative. Pluripotent stem cells within embryoid bodies can undergo differentiation in the initial embryonic development stage and cell specification along the three germ lineages of endoderm, ectoderm, and mesoderm, which comprises all somatic cell types.

This step may be conducted for 3-6 days, 4 days, 5 days, or 6 days, but without limitations thereto.

The formation and maintenance of the embryoid body within the range can allow for the maximum differentiation rate (yield) of dopaminergic neural precursor cells. When the step is conducted beyond the range, the embryoid body is badly affected and thus differentiates at a poor rate. Meanwhile, respective optimal periods of time may be established for individual types of the stem cells within the range because the working periods of time differ from one stem cell type to another.

In the step, the BMP signaling inhibitor and the activin/nodal signaling inhibitor may be added daily from the starting day of the step, whereby the efficiency of differentiation into neuroectoderm can be further improved.

Moreover, in the step, an SHH signaling activator and a GSK-3 inhibitor may be added daily from 2-6 days after the starting of the step, but without limitations thereto.

Selection may be made of various SHH signaling activators known in the art, without limitations. Examples of the SHH signaling activator include smoothened agonist (SAG), purmorphamine, halcinonide, fluticasone, clobetasol, and/or fluocinonide.

As used herein, the term "smoothened agonist" (SAG) refers to a small-molecule compound activating the sonic hedgehog (SHH) signaling pathway. SHH plays a critical role in the differentiation and distribution of dopaminergic neurons of the ventral midbrain the neuroectodermal development stage.

In addition, as explained in the following Example section, SAG acts to upregulate the expression of FOXA2, which is one of the important markers for dopaminergic neural precursor cells. FOXA2 (winged helix/forkhead box A2) (HNF3beta) is a transcription factor which plays an important role in the development of the central nervous system (CNS) and has an influence on the expression of various genes involved in midbrain-specific development and on the formation of midbrain-specific dopaminergic neurons.

Meanwhile, the use of an SHH signaling activator alone makes it impossible to differentiate stem cells into midbrain-specific dopaminergic precursor cells because an SHH signaling activator is involved, in conjunction with a GSK-3 inhibitor, in the differentiation of midbrain-specific dopaminergic precursor cells at high yield, as will described below.

SAG is represented by the following Chemical Formula 3:

[Chemical Formula 2]

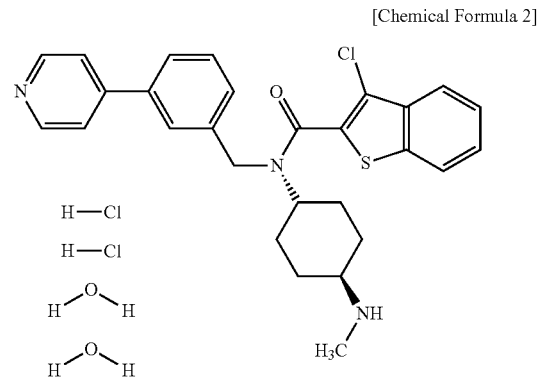

In the step, the SHH signaling activator may be used at a concentration of 0.1 to 5.0 µM, at a concentration of 0.6 to 5.0 M, or at a concentration of 1.0 µM, but without limitations thereto.

When the concentration exceeds the range, the activator may induce differentiation into undesired cells. Meanwhile, respective concentrations may be established for individual types of the stem cells within the range because the working concentration differs from one stem cell type to another.

Selection may be made of various GSK-3 inhibitors known in the art, without limitations. Particular examples of the GSK-3 inhibitor include 6-[[2-[[4-(2,4-dichlorophenyl)-5-(5-methyl-1H-imidazol-2-yl)-2-pyrimidinyl]amino]ethyl]amino]-3-pyridinecarbonitrile (CHIR99021), 3-(2,4-dichlorophenyl)-4-(1-methyl-1H-indol-3-yl)-1H-pyrrole-2,5-dione (SB216763), N6-[2-[[4-(2,4-dichlorophenyl)-5-(1H-imidazol-2-yl)-2-pyrimidinyl]amino]ethyl]-3-nitro-2,6-pyridinediamine (CHIR98014), TWS119, Tideglusib, 3-[(3-chloro-4-hydroxyphenyl)amino]-4-(2-nitrophenyl)-1H-pyrrol-2,5-dione (SB415286), (2'Z,3'E)-6-bromoindirubin-3'-oxime (BIO), valproic acid, 5-iodo-7-β-D-ribafuranosyl-7H-pyrrolo[2,3-d]pyrimidin-4-amine (Iodotubercidin), 1-azakenpaullone, curcumin, olanzapine, and/or pyrimidine.

As used herein, "CHIR99021" is a small-molecule compound activating the Wnt/beta-catenin signaling pathway (GSK-3 inhibitor). The Wnt/beta-catenin signaling pathway controls the ectoderm and neurogenesis stage and plays an important role, together with SHH, in the differentiation of midbrain dopaminergic neurons.

In addition, CHIR99021 acts to upregulate the expression of LMX1A and En-1, which are important markers for dopaminergic neural precursor cells, as illustrated in the Example section, below.

When used alone, a GSK-3 inhibitor cannot differentiate the embryoid bodies into dopaminergic neural precursor calls because the GSK-3 inhibitor is involved, in conjunction with an SHH activator, in the differentiation of midbrain-specific dopaminergic precursor calls at high yield. The use of the GSK-3 inhibitor alone may incite the embryoid bodies to increasingly develop into hindbrain cells. When continuously applied, the GSK-3 inhibitor is involved in the proliferation of the cells, but may cause a problem with safety upon transplantation.

CHIR99021 is represented by the following Chemical Formula 4:

[Chemical Formula 4]

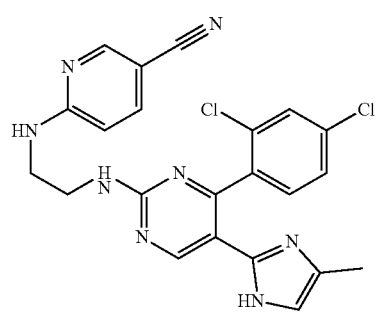

In this step, the GSK-3 inhibitor may be added at a concentration of 0.1 to 5.0 μM, at a concentration of 1.6 to 5.0 μM, or at a concentration of 2.0 μM, but with no limitations thereto.

When departing from the range, a concentration of the GSK-3 inhibitor may cause the embryoid bodies to differentiate into undesired cells. Meanwhile, respective concentrations may be established for individual types of the stem cells within the range because the working concentration differs from one stem cell type to another.

In the step, the embryoid bodies may be cultured in bFGF-free ES cell culture medium. However, so long as it allows EB to be cultured therein, any culture medium may be selectively used without limitations.

Step c)

This step is a process in which neural rosettes are formed. In this process, selection can be made of the cells that are fated to differentiate into neural cells among the neuroectodermal cells.

As used herein, the term "neural rosette" refers to a cluster of cells that are fated to develop into various types of neural cells.

The step may be conducted for 3-6 days, 4 days, or 5 days, but without limitations thereto.

When the step is conducted for a period of time departing from the range, neural rosettes are not maintained to cease the differentiation or to cause the differentiation to proceed in an undesired direction. Meanwhile, respective optimal periods of time may be established for individual types of the stem cells within the range because the working periods of time differ from one stem cell type to another.

In the step, an SHH signaling activator and a GSK-3 inhibitor may be added daily from the starting of the step. In this process, the cells fated to differentiate into dopaminergic neural precursor cells, other than general neural rosettes that can differentiate into various types of neural cells, can be obtained in a large amount.

In the step, the cells are cultured in a DMEM/F12 cell culture medium. However, so long as it allows the formation/maintenance of neural rosettes, any medium may be selectively employed without limitations thereto.

The cell culture medium may further comprise N2 supplement CTS, human insulin, and bFGF.

Step d)

This step is a process in which neural rosettes are differentiated into dopaminergic neural precursor cells. In this process, selection is made of neural rosettes only, with the exclusion of differentiated cells other than neural cells, thereby reinforcing differentiation into dopaminergic neural precursor cells.

As used herein, the term "neural cell" refers to a cell that is a component of the nervous system and is interchangeably used with neuron.

As used herein, the term "dopaminergic neural cell" refers to a neural cell secreting the neurotransmitter dopamine.

The term "precursor cell", as used herein, refers to a cell that can be divided just before expressing traits of the cell that has undergone complete differentiation and is interchangeably used with "progenitor" or "precursor".

In the present disclosure, therefore, "dopaminergic neural precursor cells" are cells that can be divided into neural cells secreting dopamine after experiencing a maturation stage since in vivo transplantation.

The step may be conducted for 8-10 days or 9 days, but with no limitations thereto.

When the step is conducted for less than the lower limit of the range, the differentiation rate of dopaminergic precursor cells may decrease. A period of time greater than the upper limit of the range may make mass production impossible. Meanwhile, respective optimal periods of time may be established for individual types of the stem cells within the range because the working periods of time differ from one stem cell type to another.

In the step, an SHH signaling activator and a GSK-3 inhibitor may be added daily from the starting of the step. In this process, most (about 80% or more) of the cells can differentiate into dopaminergic neural precursor cells with the lapse of differentiation days.

The step is conducted by exchanging the medium with a fresh medium every day and passaging the cells every three days from the starting of the step, whereby the dopaminergic neural precursor cells can be proliferated on a large scale and maintained in the best state and the differentiation rate can be improved.

In the step, the cells are cultured in a DMEM/F12 cell culture medium. However, so long as it allows the formation/maintenance of dopaminergic precursor cells, any medium may be selectively employed without limitations thereto.

The cell culture medium may further comprise N2 supplement CTS and B-27 supplement CTS.

The method may further comprise the following step:

e) proliferating the dopaminergic neural precursor cells through passage.

Step e)

This step is a process in which the dopaminergic neural precursor cells are produced in a large amount by proliferation. This process can make stable cell supply possible as well as increasing the differentiation rate of dopaminergic neural precursor cells.

The differentiation rate to dopaminergic neural precursor cells, induced by the method, may be 80% or greater, but is not limited thereto.

The dopaminergic neural precursor cells induced by the method may improve in the expression level of FOXA2, LMX1A, and/or En1.

According to an embodiment of the present disclosure, the dopaminergic neural precursor cells induced by the method may alleviate symptoms of Parkinson's disease.

The cell culture in each step of the method may further comprise an extracellular matrix (ECM). This is because undifferentiated stem cells and neural cells cannot be attached to the culture dish by themselves, but can be maintained and cultured with the aid of an extracellular matrix or feeder cells.

The extracellular matrix may be, for example, laminin, but is not limited thereto. In addition to laminin, other extracellular matrices may be used alone or in combination. Suitable extracellular matrices may differ from one type of stem cells to another.

The extracellular matrix may be used at a concentration of 3.5-5.5 µg/mL, 4.0 µg/mL, or 5.0 µg/mL, but without limitations thereto.

When the concentration of the extracellular matrix exceeds the range, differentiation into dopaminergic neural precursor cells may be impossible or a problem with adhesion may occur, causing problems in the production process.

The neural precursor cells obtained by the method may be used to treat neurodegenerative diseases, for example, Alzheimer's disease, Huntington's disease, Parkinson's disease, and amyotrophic lateral sclerosis.

Another aspect of the present disclosure pertains to a method for mass production of dopaminergic neural precursor cells, the method comprising the following steps:

a) culturing stem cells;
b) forming and maintaining an embryoid body;
c) generating a neural rosette;
d) differentiating the neural rosette into dopaminergic neural precursor cells; and
e) proliferating the dopaminergic neural precursor cells through passage.

As for the method for mass production of dopaminergic neural precursor cells, its descriptions in common with the method for inducing differentiation into dopaminergic neural precursor cells are omitted in order to avoid undue redundancy leading to the complexity of this specification.

A better understanding of the present disclosure may be obtained through the following examples which are set forth to illustrate, but are not to be construed as limiting the present disclosure.

Culturing of Human Embryonic Stem Cells (hESCs)

Undifferentiated hESCs (SNU32, the Korean Cell Line Bank) to be differentiated into dopaminergic neural cells were cultured in a CELLstart-coating dish containing a TeSR2 (STEMCELL, SCR5860) medium.

In this regard, the undifferentiated stem cells were cultured in a monolayer format. Under the principle of 7-day culturing, cells were harvested using a scraper after incubation with Versene (GIBCO, 15040-066) for 4 minutes in a 37° C. incubator when reaching a confluency of 90-95% and then transferred into a 15-ml tube. The cells were pipetted about 8-12 times with a 1000P pipette before passage at 1:7 ratio (based on CELLstart-CTS coating dish), and then maintained with the medium exchanged with afresh medium daily within 24 hours every day for 7 days.

Culturing of Induced Pluripotent Stem Cells (iPSCs)

Undifferentiated iPSCs (hFSiPS1, the National Stem Cell Bank, Depository Authority: Division for Intractable Disease at the Korean National Institute of Health) to be differentiated into dopaminergic neural cells were cultured in the same manner as the hESC culturing method.

Immunocytochemistry Assay

Cells were fixed for 10 min in a 4% paraformaldehyde solution.

In order to smoothly penetrate into the cytoplasm, each antibody was incubated with 0.1% Trition X-100 (in PBS) for 15 min and then with 2% bovine serum albumin (BSA, in PBS) for 1 hour at room temperature.

Subsequently, the primary antibodies (see Table 1, below) were allowed to bind to the cells at 4° C. Secondary antibodies suitable for the respective primary antibody species (see Table 1, below) were used to confirm the primary antibody-bound cells.

Finally, cell nuclei were imaged. In this regard, the cells were incubated with 4', 6-diamino-2-phenylindole (DAPI) in PBS for 10 min to stain the nuclei which were then imaged under a fluorescence microscope. Important markers were identified and analyzed.

TABLE 1

| Protein | Species | Manufacturer | Cat. No. | Dilution |
| --- | --- | --- | --- | --- |
| LMX1A | Goat | Santa Cruz | sc-54273 | 1:100 |
| FOXA2 (HNF3beta) | Mouse | Santa Cruz | sc-374376 | 1:50 |

Gene Expression Assay (qRT-PCR)

Cells were harvested from which total RNA was then isolated using the Easy-Spin® Total RNA extraction kit (iNtRON Biotechnology). cDNA was synthesized from 1 µg of the total RNA, using the PrimeScript™RT Master Mix (TAKARA Bio Inc.). mRNA levels were quantitated by real time RT-PCR using SYBR®Premix Ex Taq™ (TAKARA Bio Inc.) and CFX96 Real-Time System (Bio-Rad). Primer sequences used in the gene expression assay are given in Table 2, below.

TABLE 2

| Gene Name | Sequence (5'-3') |
| --- | --- |
| En-1 (Engrailed 1) | F: CGT GGC TTA CTC CCC ATT TA (SEQ ID NO: 1)<br>R: TCT CGC TGT CTC TCC CTC TC (SEQ ID NO: 2) |
| GAPDH (Glyceraldehyde-3-Phosphate Dehydrogenase) | F: CAA TGA CCC CTT CAT TGA CC (SEQ ID NO: 3)<br>R: TTG ATT TTG GAG GGA TCT CG (SEQ ID NO: 4) |

Example: Protocol for Differentiation into Dopaminergic Neural Precursor Cell

After being stabilized through two passage rounds from the time of thawing an MCB (Master Cell Bank), the hESCs or iPSCs cultured above were subjected to the 3$^{rd}$ passage to induce differentiation into dopaminergic neural precursor cells on the passage culture dish.

Starting from the day (d0) on which the 3$^{rd}$ passage culture dish was prepared, the cells were pre-treated with 5 µM dorsomorphin (hereinafter referred to as "DM") (Millipore, 171260) and 5 µM SB431542 (hereinafter referred to as "SB") (Sigma, S4317) in a hESC culture medium (TeSR2, STEMCELL, SCR5860) for two days from differentiation day 6 (d6) to differentiation day 8 (d8) to increase the feasibility of differentiation into neuroectoderms.

On differentiation day 8 (d8), the hESCs that were being cultured in a monolayer format were subdivided into a format of 1.5-mm grids by using 1-ml 26-G syringe and then left for about 30 min in a 37° C. incubator or incubated with 2 ml of collagenase (Animal Origin Free (CLSAFC), Worthington, LS004138) for about 5 min in a 37° C. incubator to form a 1.5-mm square cell sheet which acts as a basis for embryoid bodies, thereby forming embryoid bodies (hereinafter referred to as "EM"). The EM thus induced was cultured in a bFGF-free hESC culture medium (EB medium). In this regard, while being incubated for 4 days until differentiation day 12 (d12), the cells pretreated with 5 μM DM and 5 μM SB were further pretreated with the patterning factors, 1.0 μM SAG (Millipore, 566661, hereinafter referred to as "SAG") and 2.0 μM CHIR99021 (Milteny, 130-106-539), to increase the occupancy degree of midbrain dopaminergic neural precursor cells.

On differentiation day 12 (d12), a DMEM/F12 medium supplemented with 20 μg/nL human insulin and 20 ng/mL bFGF (mN2+b) was used to attach the EB formed in the previous step to a Laminin-521-coating culture dish (pEB step), followed by incubation with the patterning factors 1.0 μM SAG (smoothened agonist) and 2.0 μM CHIR99021 for 5 days.

On differentiation day 17 (d17), neural rosettes formed from the attached EB were separated by treating with Accutase (Millipore, SCR003) for 2 min or using a method in which a user processed a glass pipette and directly separate the cells therewith. The neural rosettes were then re-attached to a separate Laminin-521-coating culture dish. For use in the re-attachment, DMEM/F12 medium supplemented with N2 (N-2 supplement, CTS grade, GIBCO, A1370701, hereinafter referred to as "N2") and B-27 (B-27 supplement xeno-free, CTS grade, GIBCO, A1486701, hereinafter referred to as "B27") (N2B27 medium), which is used as a medium for culturing dopaminergic neural precursor cells, was added with 1.0 μM SAG and 2.0 μM CHIR99021. For re-attachment, the medium was further added with 10 μM Y27632 and then used to aid the attachment of the cells for one hour. After one hour, the medium was exchanged with Y27632-free one. Until day 20 (d20), the medium was exchanged daily with afresh medium within 24 hours to continuously induce differentiation into dopaminergic neural precursor cells. When treated with Accutase, all of the cells, except for neural rosettes, were separated and removed. Only the neural rosette dusters were transferred to 15-ml tubes by using a scraper and dissociated by pipetting up and down about 40 times with a 200P pipette before re-attachment onto a Laminin-521-coating culture dish.

On differentiation day 20 (d20), the dopaminergic neural precursor cells were separated into single cells in the presence of Accutase and re-attached at a density of $4.0 \times 10^6$ cells/35 mm dish onto a Laminin-521-coating culture dish containing an N2B27 medium supplemented with 1.0 μM SAG and 2.0 μM CHIR99021. While the medium was exchanged every day with a fresh medium, the cells were re-attached at a density of $4.0 \times 10^6$ cells/35-mm dish every three days in a Laminin-521-coating culture dish to proliferate the cells in a large amount before preparing a working cell bank (WCB) on day 26 (d26).

[Clinical entry] Dopaminergic neural precursor cells in the WCB prepared on day 26 were dissociated into single cells by using Accutase in the same manner as in the re-attachment method. The dissociated single cells were aliquoted into vials at a density of $3.0 \times 10^6$ cells/vial or in a range guaranteed by a cryoprotectant.

[Preparation of transplant cells] The WCB was used 9 days after being thawed. For a 35-mm culture dish, $4.0 \times 10^6$ cells are needed. Thus, 2 vials ($3.0 \times 10^6$ cells for each vial) were pooled and living cells were counted with a trypan blue solution. Among them, $4.0 \times 10^8$ cells were attached to a 35-mm Lamnin-521 coating culture dish containing the N2B27 medium and cultured until differentiation day 35 (d35), with the medium exchanged every day with afresh medium. Also, the differentiation induction and proliferation was conducted by reattachment every three days until day 35 (d35).

A concrete protocol is illustrated in FIG. 1.

Experimental Example 1: Step of Culturing Stem Cell 1-1. Optimal Time of Treatment with DM and SB431542

The same procedure as in the method according to the present disclosure was conducted, with the exception of treatment with DM and SB431542 from culturing day 8, instead of culturing day 6.

Figure 2A:
FIGS. 2a and 2b are images showing an optimal duration of stem cell culturing according to an embodiment of the present disclosure (derived from embryonic stem cells)
Figure 2A:
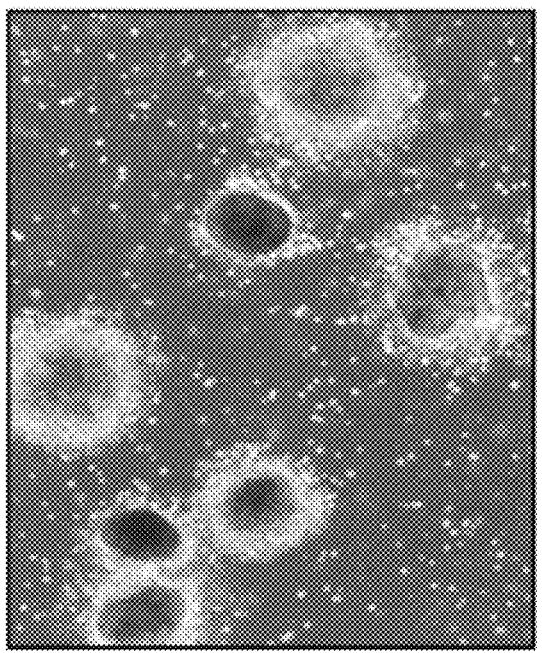

As can be seen in FIG. 2a, treatment with DM and SB431542 from culturing day 6 accounting for a stem cell culturing step (the method of the present disclosure) guaranteed better results in terms of neural rosette state and yield, than treatment with DM and SB431542 from culturing day 8 accounting for an embryoid body forming step (conventional method).

This result suggests that pre-treatment with DM and SB431542 from the undifferentiated cell stage prior to the embryoid body formation can increase the feasibility of differentiation into neuroectoderm upon embryoid body formation as well as exceptionally improving the final rate of differentiation into dopaminergic neural precursor cells.

1-2. Optimal Culturing Duration

The same procedure as in the method according to the present disclosure was conducted, with the exception that following pretreatment with DM and SB431542 from culturing day 7 to culturing day 9, grids for embryoid body formation were established on culturing day 9, instead of the establishment of grids for embryoid body formation on culturing day 8.

Figure 2B:
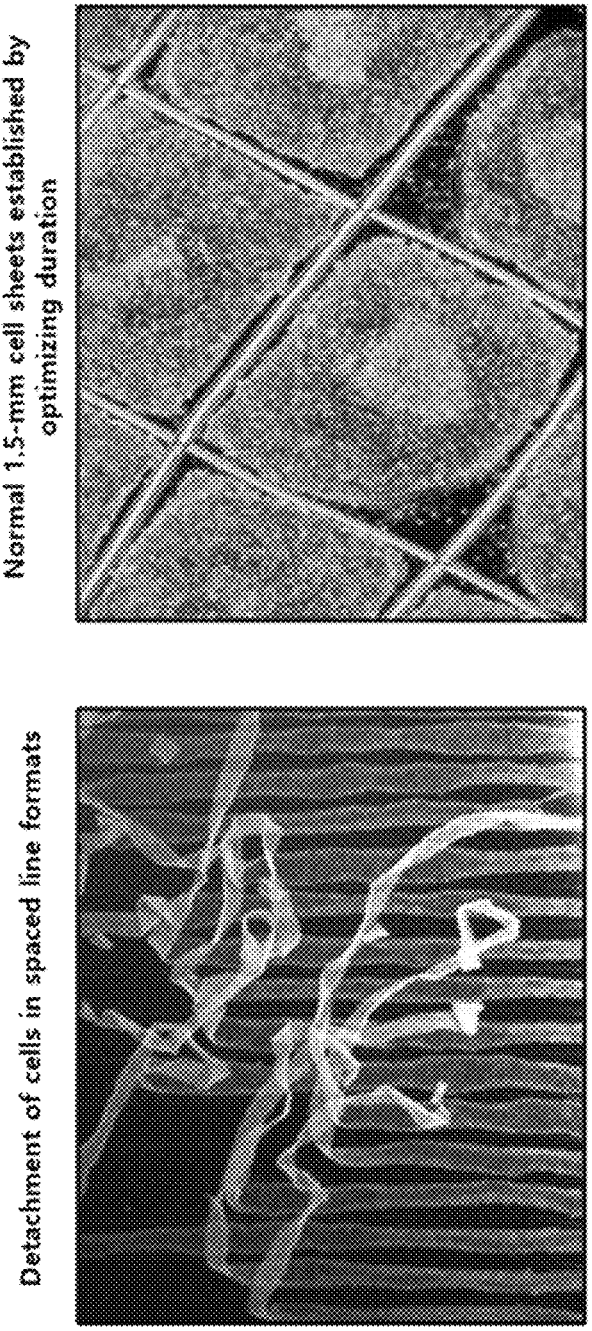

As can be seen in FIG. 2b, when lines were drawn after formation of embryoid bodies on culturing day 9, the cells were floated on the medium because their adhesion became very weak. The cells were detached from the bottom of the culture dish before establishment of grids and were difficult to form into 1.5-mm square cell sheets (the left panel in FIG. 2b). In contrast, when grids for embryoid body formation were established on culturing day 8 (the method of the present disclosure), 1.5-mm cell sheets could be normally made (the right panel in FIG. 2b).

Experimental Example 2: Step of Forming and Maintaining Embryoid Body 2-1. Optimal Culturing Duration The same procedure as in the method according to the present disclosure was conducted, with the exception that EB formation was induced by treatment with DM and SB431542 until culturing day 13, instead of attachment of EB to the culture dish on culturing day 12 (on day 4 of EM formation/maintenance).

Figure 3:
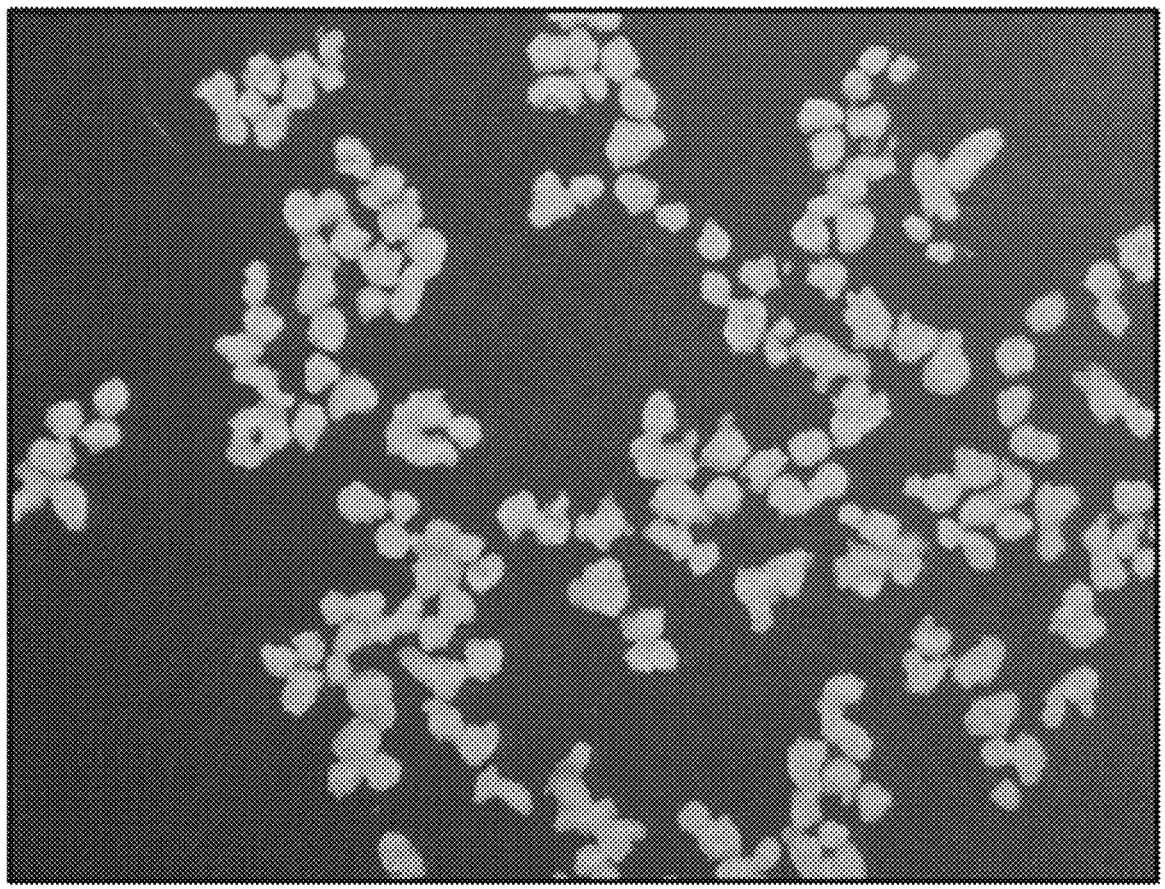
FIG. 3 is an image showing an optimal duration of embryoid body culturing according to an embodiment of the present disclosure (derived from embryonic stem cells)

As shown in FIG. 3, embryoid bodies were, in the most part, individually maintained well until day 4 (culturing day 12), but since day 5 (culturing day 13), embryoid bodies were attached to each other to form large aggregates at high frequency.

2-2. Optimal Time of Treatment with SAG and CHIR99021

The same procedure as in the method according to the present disclosure was conducted, with the exception of treatment with SAG and CHIR99021 from culturing day 6 or 8, instead of treatment with SAG and CHIR99021 from culturing day 10.

Figure 4A:
FIGS. 4a, 4b and 4c are images showing an optimal time of treatment with SAG and CHIR99021 for embryoid body culturing according to an embodiment of the present disclosure (derived from embryonic stem cells)
Figure 4B:
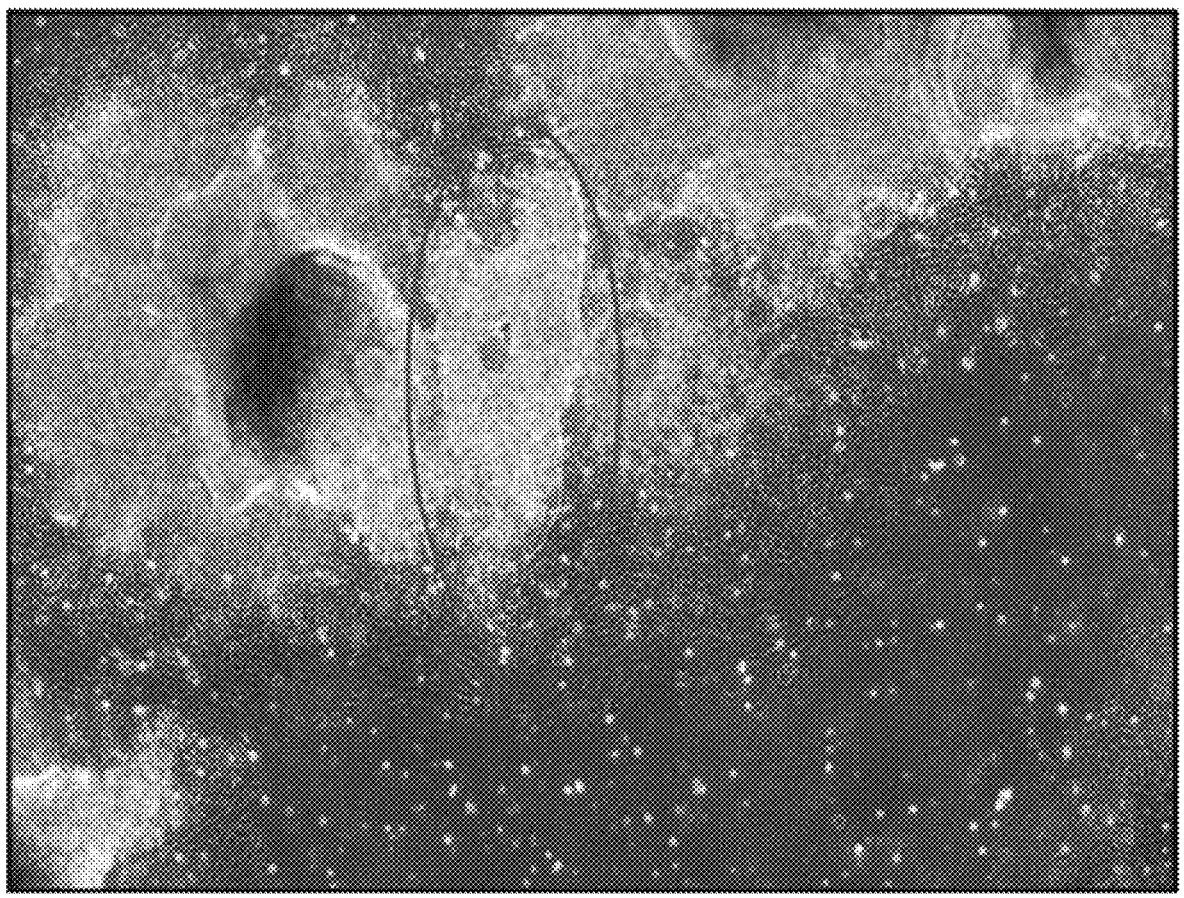
Figure 4C:
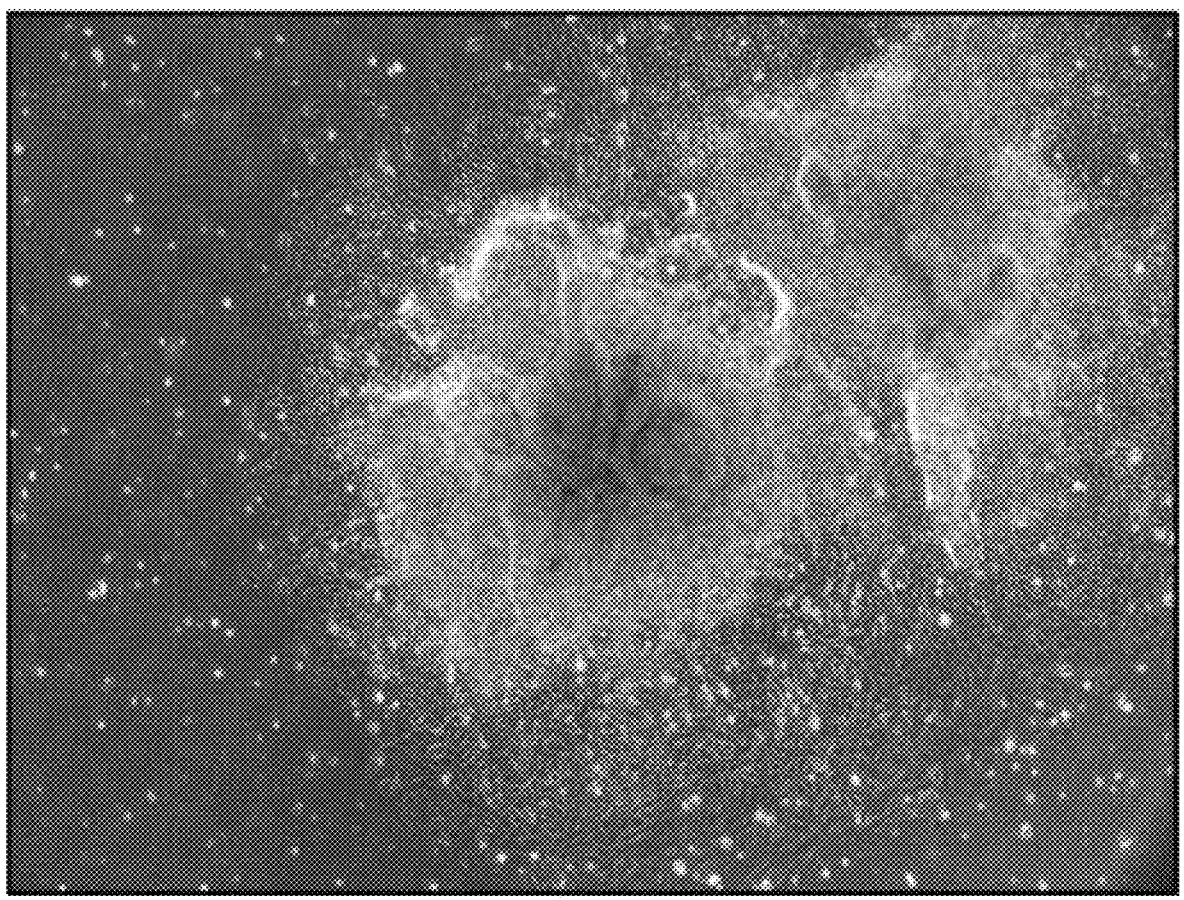

As can be seen in FIGS. 4a to 4c, neural rosettes were not normally formed and different morphologies of differentiated cells were redundantly found after treatment with SAG and CHIR99021 from differentiation day 6 (FIG. 4a). The neural rosettes that had been treated with SAG and CHIR99021 from differentiation day 8 were morphologically collapsed and showed a bad condition (FIG. 4b), compared to those treated with SAG and CHIR99021 from day 10 (FIG. 4c).

2-3. Comparison of Monolayer Differentiation

Examination was made to show whether or not the culturing/differentiation process could be simplified. In this regard, differentiation into dopaminergic neural precursor cells was carried out using the same protocol as the method of the Example, with the exception of omitting the embryoid body formation procedure (culturing days 8 to 12). Comparison between the conventional method and the method of the present disclosure was made with respect to the expression of FOXA2 and/or LMX1A on differentiation day 27.

Figure 5A:
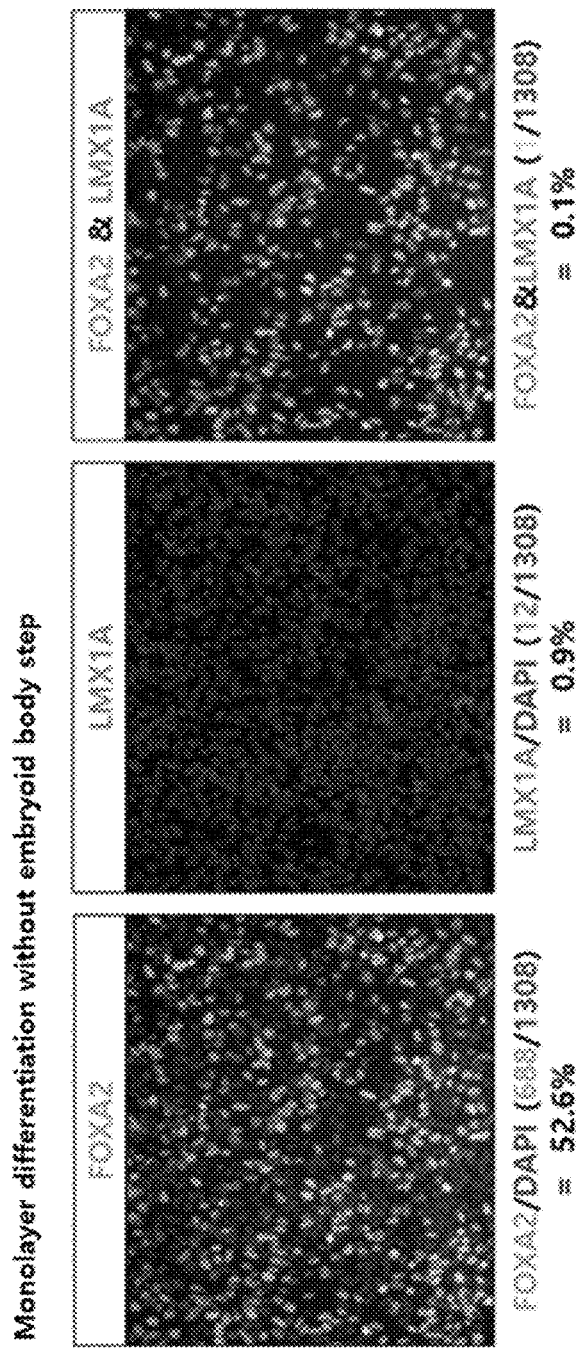
FIGS. 5a and 5b are images showing whether or not the step of forming embryoid bodies are necessary according to an embodiment of the present disclosure (derived from embryonic stem cells)
Figure 5B:
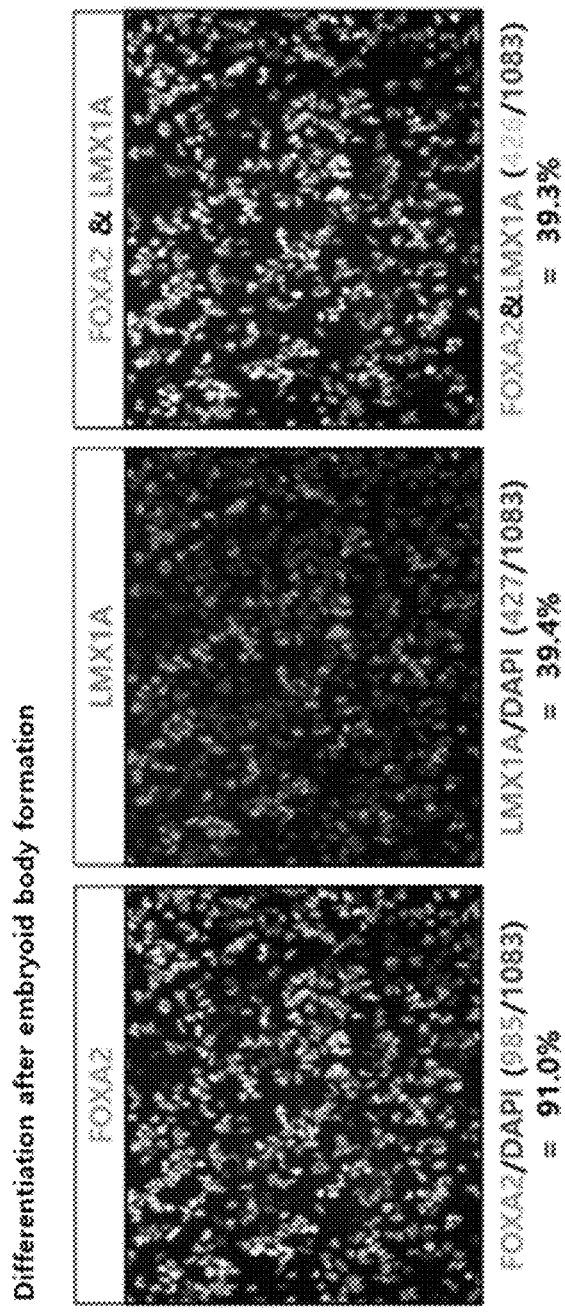

As seen in FIGS. 5a and 5b, differentiation into neuroectoderms in a monolayer format without embryoid body formation (FIG. 5a) resulted in significantly low expression levels of FOXA2 and/or LMX1A, compared to differentiation with embryoid body formation (the method of the present disclosure, FIG. 5b).

Experimental Example 3: Step of Generating Neural Rosette 3-1. Optimal Differentiation Duration The same procedure as in the method of the present disclosure was conducted, with the exception that neural rosettes were generated until culturing day 18 (neural rosette generation day 6), instead of re-attachment of neural rosettes onto a separate culture dish on culturing day 17 (neural rosette generation day 5).

Figure 6:
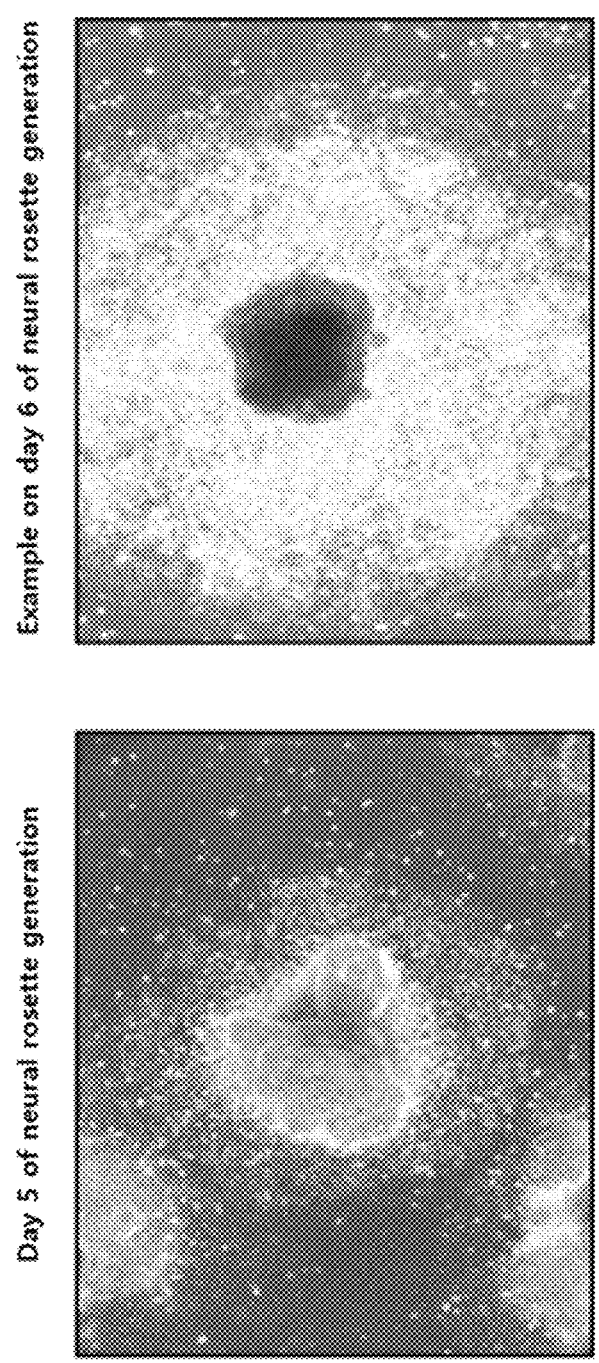
FIG. 6 shows images illustrating an optimal duration of culturing for neural rosette generation (derived from embryonic stem cells)

As shown in FIG. 6, neural rosettes were maintained and proliferated in a good state until neural rosette generation day 5 (the method of the present disclosure). On day 6, however, the neural rosettes underwent a whitening phenomenon starting from the outer part thereof at high frequency. In addition, the central part of each rosette turned black while the cells were morphologically changed. That is, most of the cells were dead and spontaneously detached off upon washing with PBS or upon medium exchange. Therefore, there is a difficulty in supplying neural rosettes.

Meanwhile, the formation of neural rosettes during the proliferation of neural precursor cells is an initial check point of determining whether differentiation into neuroectoderms and midbrain dopaminergic neural cells was successfully induced. The quantity of rosettes and the duration of rosette maintenance are very important in forming and quantitatively securing midbrain dopaminergic neural precursor cells in future.

Experimental Example 4: Step of Differentiation into Dopaminergic Neural Precursor Cells 4-1. Optimal Duration of Differentiation In order to establish the preparation time of WBC which guarantees the highest rate of differentiation into dopaminergic neural precursor cells, WCB was established on culturing day 23, instead of culturing day 26. With respect to the final rate of differentiation into dopaminergic neural precursor cells, comparison between this method and the method of the present disclosure was made.

Figure 7A:
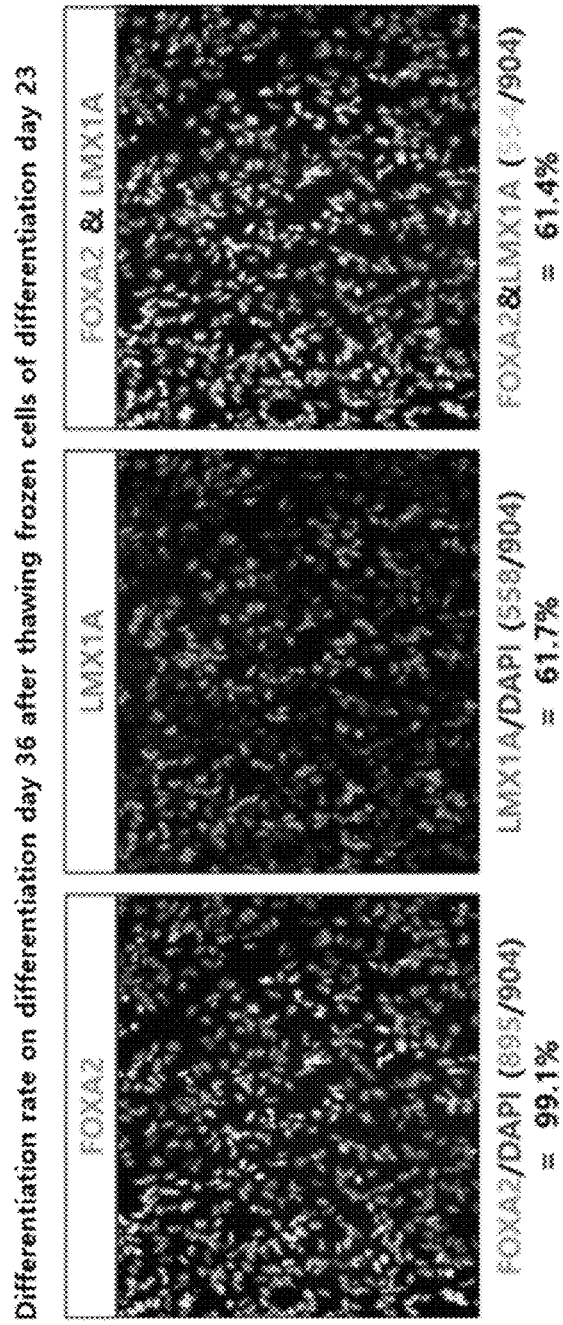
FIGS. 7a and 7b are images showing an optimal duration of culturing for differentiation into dopaminergic neural precursor cells according to an embodiment of the present disclosure (derived from embryonic stem cells)
Figure 7B:
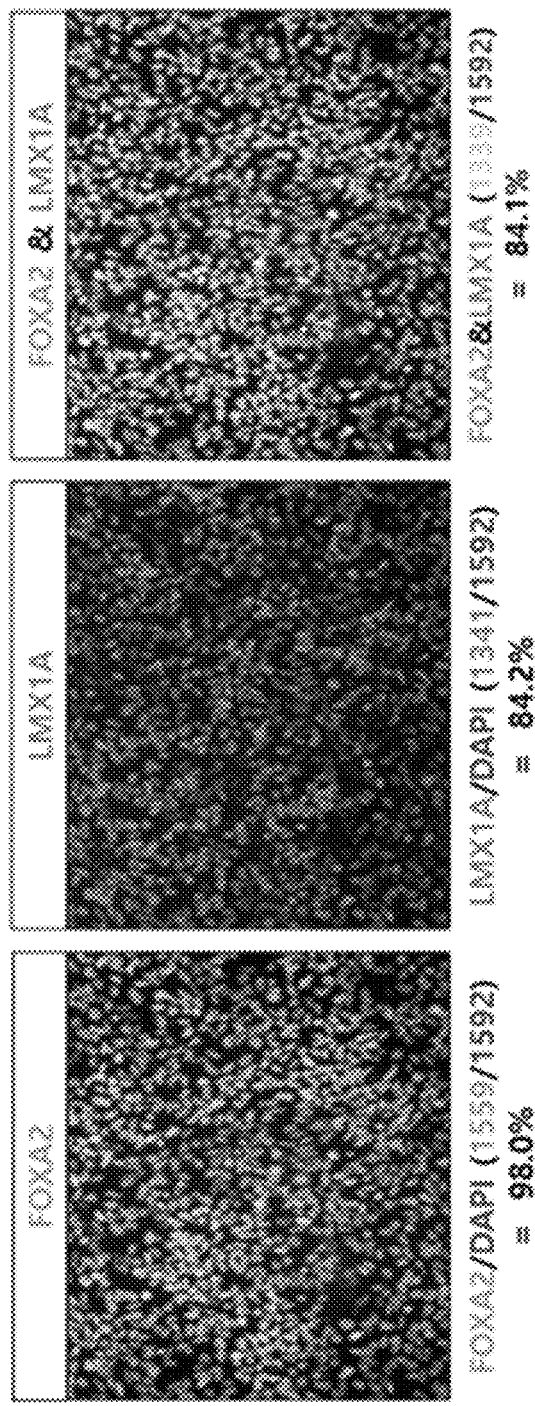

As can be seen in FIGS. 7a and 7b, a lower differentiation rate was measured in the case where a WCB was established and thawed on day 23 (FIG. 7a), compared to the case where a WCB was established and thawed on day 26 (the method of the present disclosure, FIG. 7b).

4-2. Optimal Duration of Treatment with SAG and CHIR99021

The cells were differentiated into dopaminergic neural precursor cells in the same procedure as the method of the present disclosure was conducted, with the exception of treatment with SAG and CHIR99021 until culturing day 20 or 35, instead of treatment with SAG and CHIR99021 until culturing day 26. With respect to En1 expression and cell morphology, the method was compared to the method of the present disclosure.

Figure 8A:
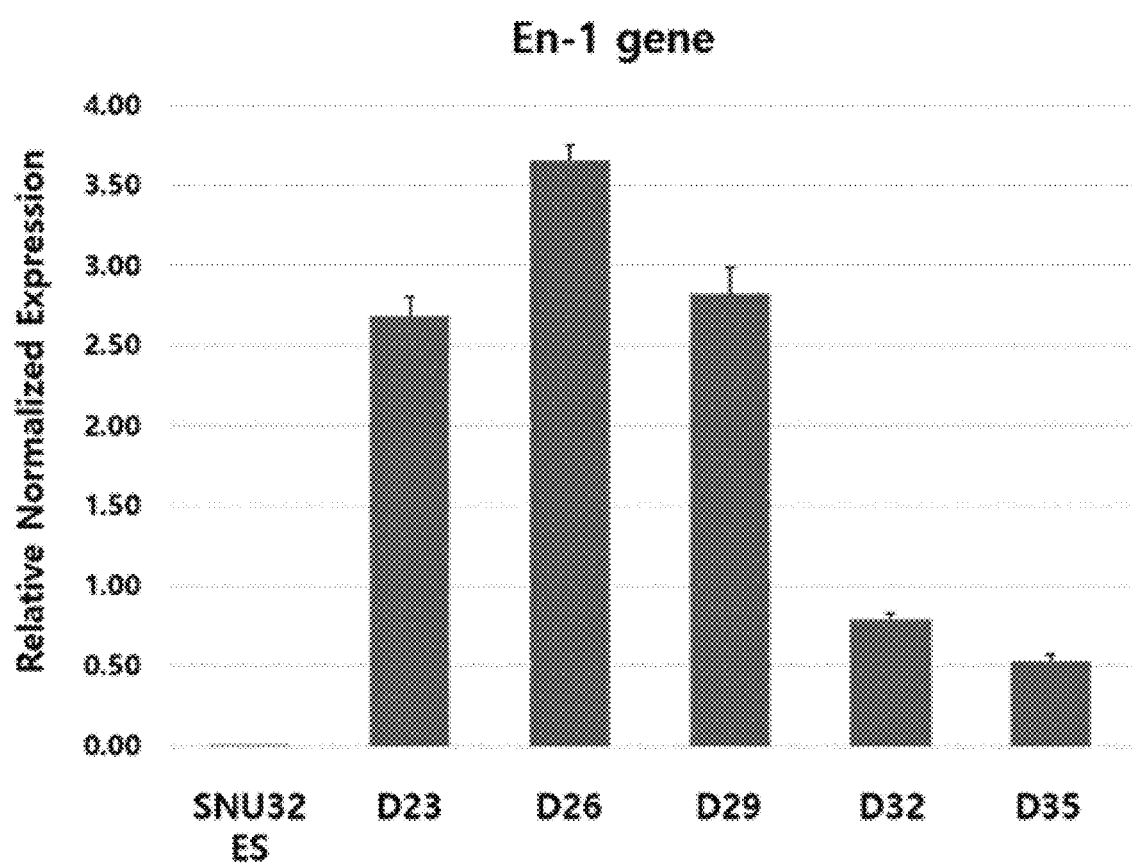
FIGS. 8a, 8b, 8c and 8d are graphs and images showing an optimal duration of treatment with SAG and CHIR99021 for differentiation into dopaminergic neural precursor cells according to an embodiment of the present disclosure (derived from embryonic stem cells)
Figure 8B:
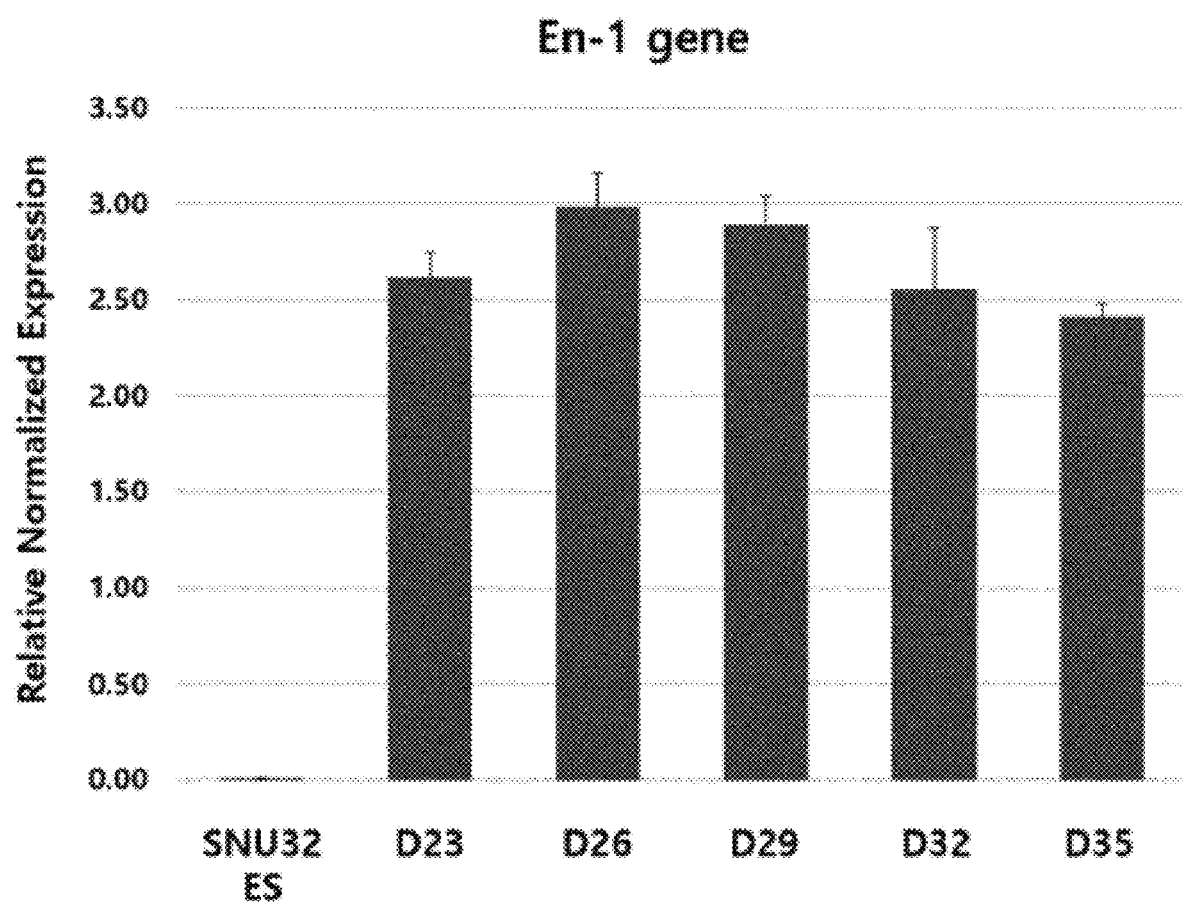
Figure 8C:
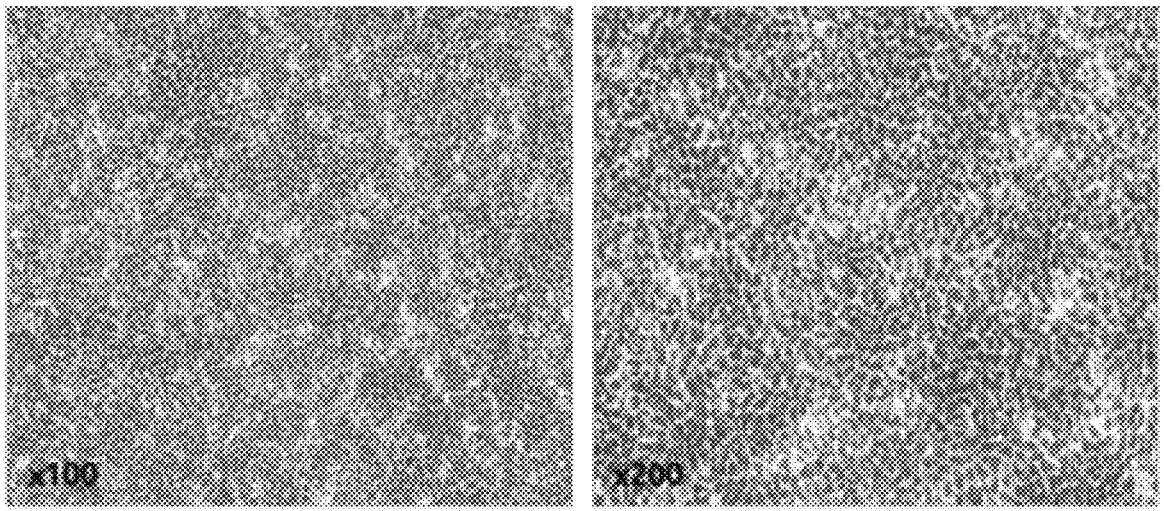
Figure 8C:
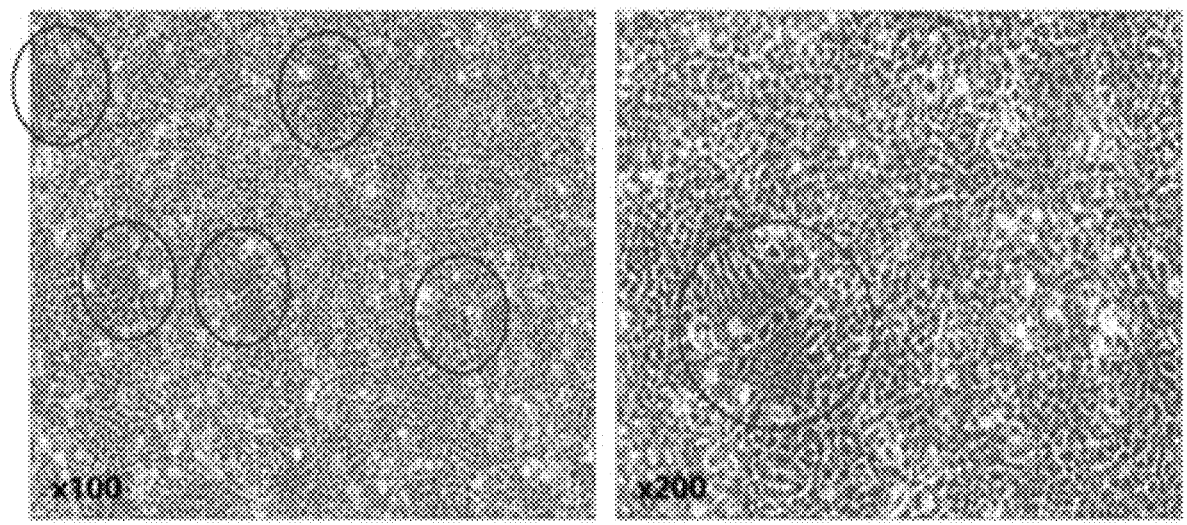
Figure 8D:
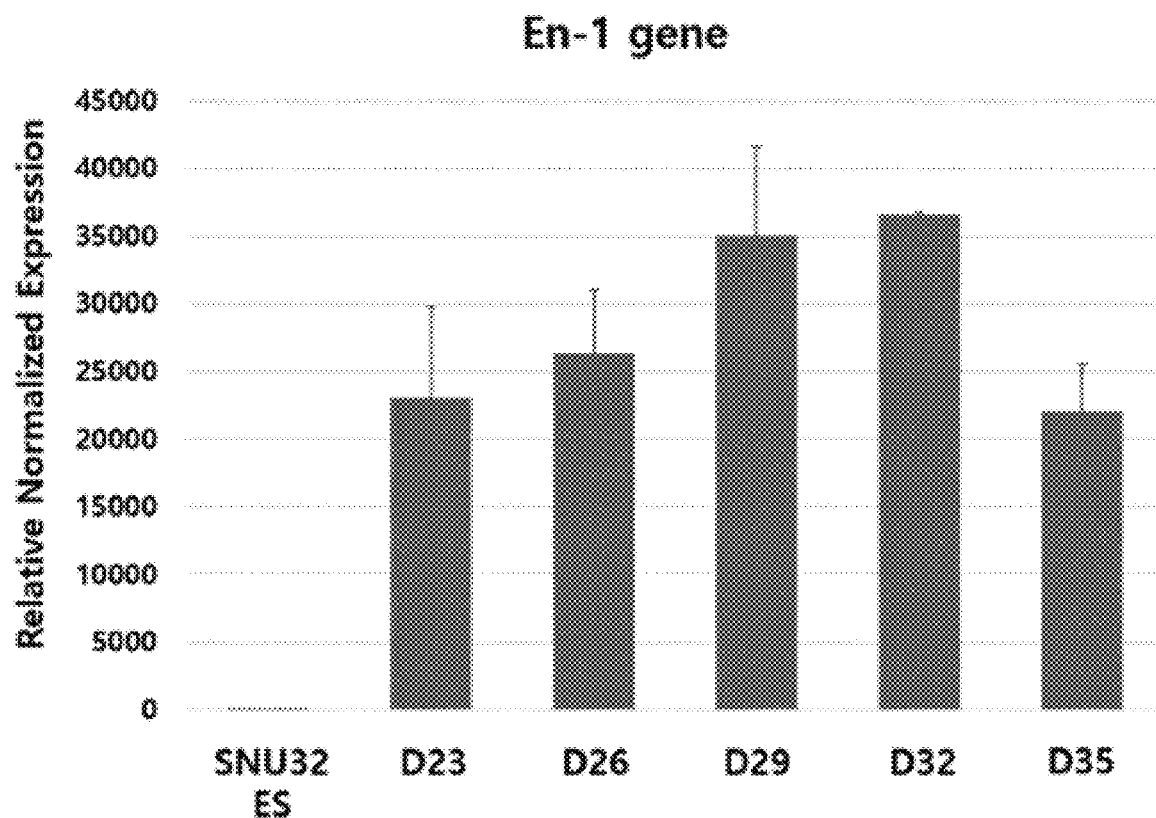
Figure 8D:
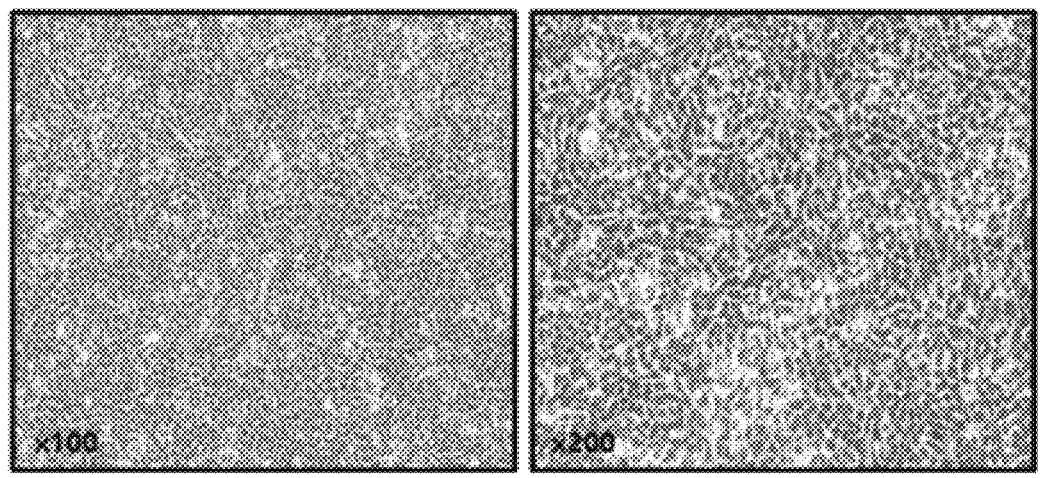

As shown in FIGS. 8a to 8d, the cells treated with SAG and CHIR99021 until day 20 (FIG. 8a) were measured to more rapidly decrease in En1 expression level with the progression of differentiation, compared to the cells treated with SAG and CHIR99021 until day 35 (FIG. 8b). In addition, as can be seen in FIG. 8c, the cells treated with SAG and CHIR99021 until day 35 started to take more mature morphology in which differentiation was further proceeded from dopaminergic neural precursor cells while not decreasing in proliferative rate. In contrast, the cells treated with SAG and CHIR99021 until day 26 (the method of the present disclosure, FIG. 8d) was found to exhibit a lower reduced expression level of En1 and take a precursor cell morphology. Hence, selection was made of the method in which the cells are treated with SAG and CHIR99021 until day 26 (FIG. 8d).

Experimental Example 5: Optimal Concentration of SAG and CHIR99021

The cells were differentiated into dopaminergic neural precursor cells in the same manner as the method of the present invention, with the exception of treating the cells with SAG and CHIR99021 at respective concentrations of 0.5 μM and 1.0 μM, or 1.0 μM and 1.5 μM, instead of 1.0 μM and 2.0 μM. With the expression of FOXA2 and/or LMX1A, this method was compared to the method of the present disclosure.

Figure 9A:
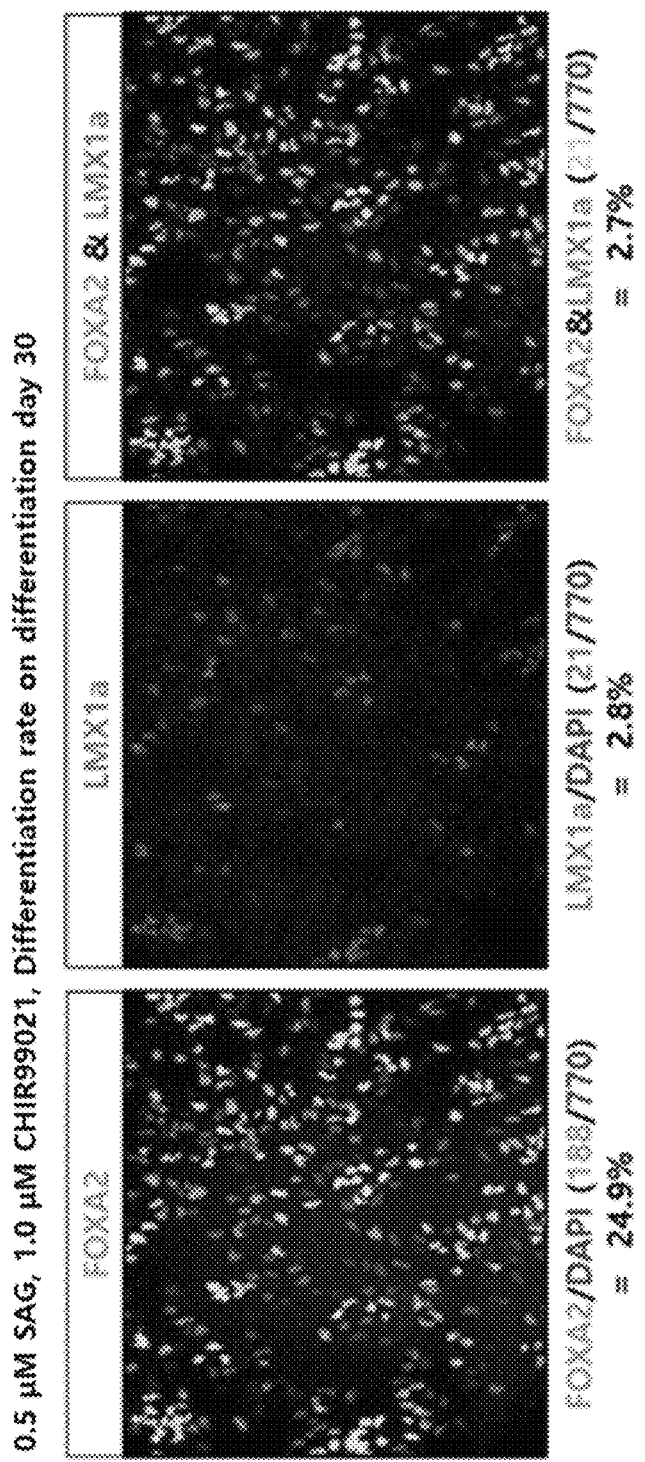
FIGS. 9a, 9b and 9c are images showing optimal treatment concentrations of SAG and CHIR99021 according to an embodiment of the present disclosure (derived from embryonic stem cells)
Figure 9B:
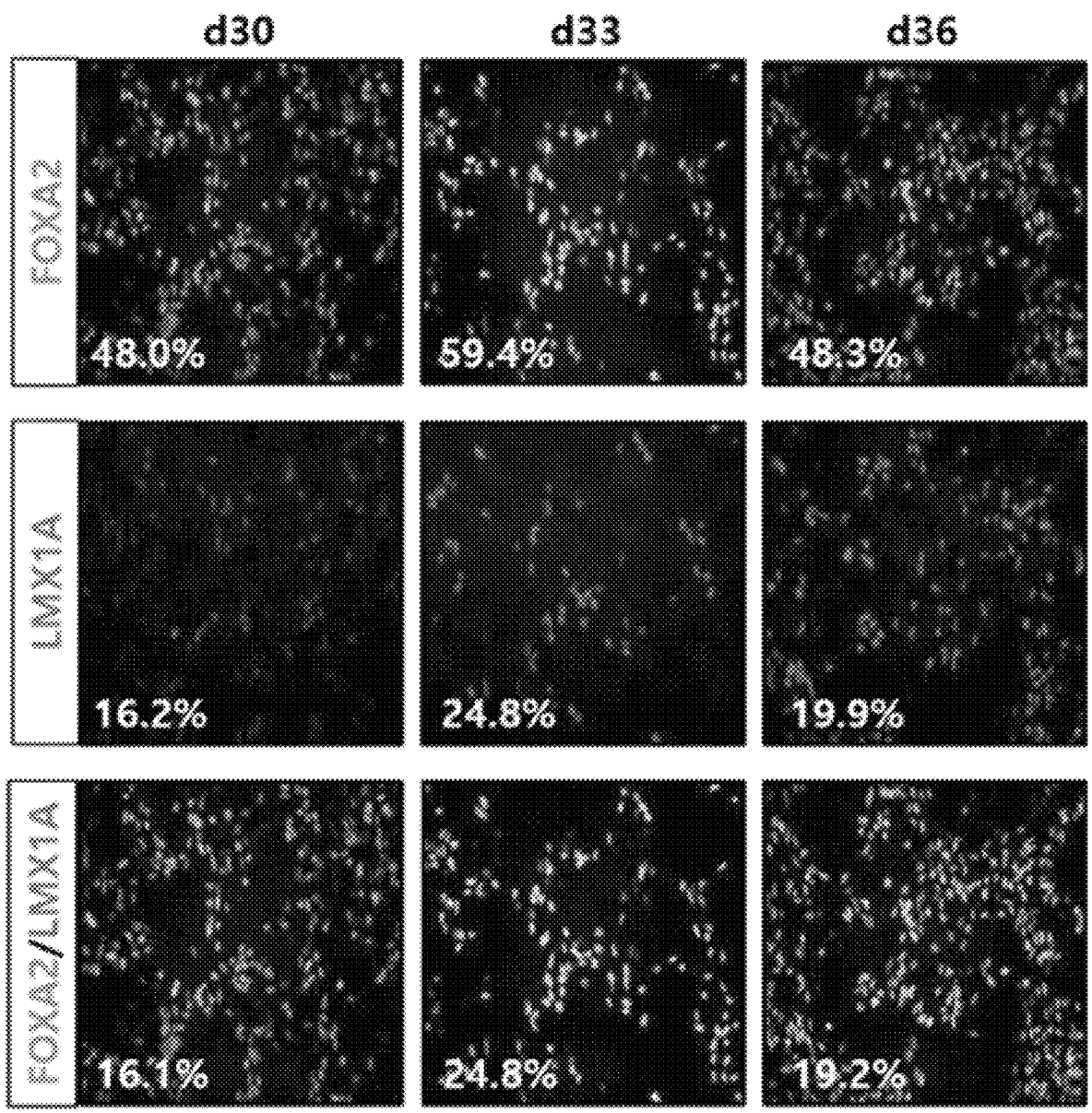
Figure 9C:
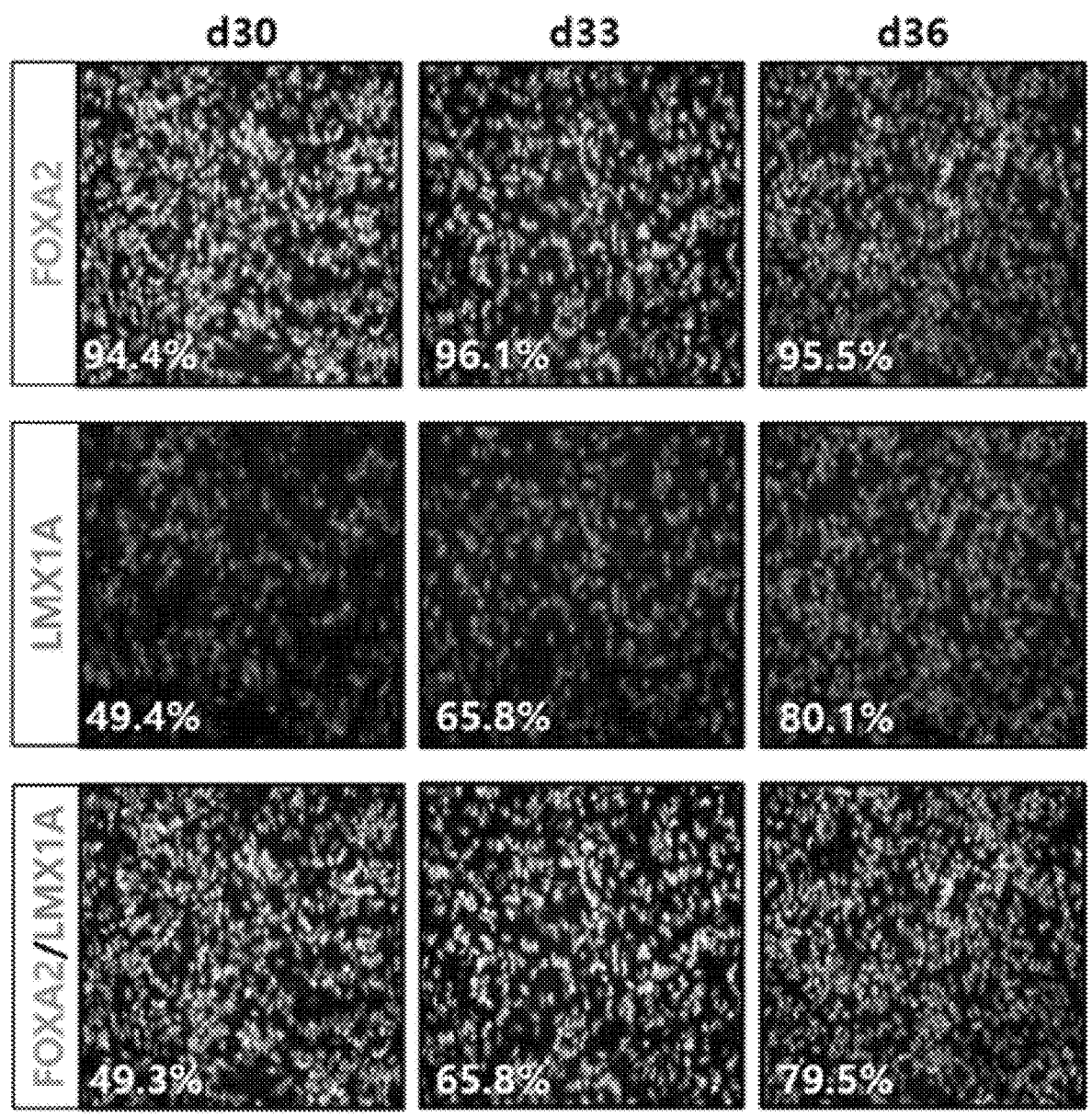

As seen in FIGS. 9a to 9c, higher expression levels of FOXA2 and/or LMX1A were detected in the cells treated with SAG and CHIR99021 at respective concentrations of 1.0 μM and 2.0 μM (the method of the present disclosure, FIG. 9c), compared to the cells treated with SAG and CHIR99021 at respective concentrations of 0.5 μM and 1.0 μM (FIG. 9a) or 1.0 μM and 1.5 μM (FIG. 9b).

Experimental Example 6: Optimal Concentration of ECM

With respect to CELLstart and various concentrations (2-7 μg/mL) of ECM (Laminin 521), stem cells were cultured using the same protocol as in the above Examples to conduct a cell adhesion test.

Figure 10A:
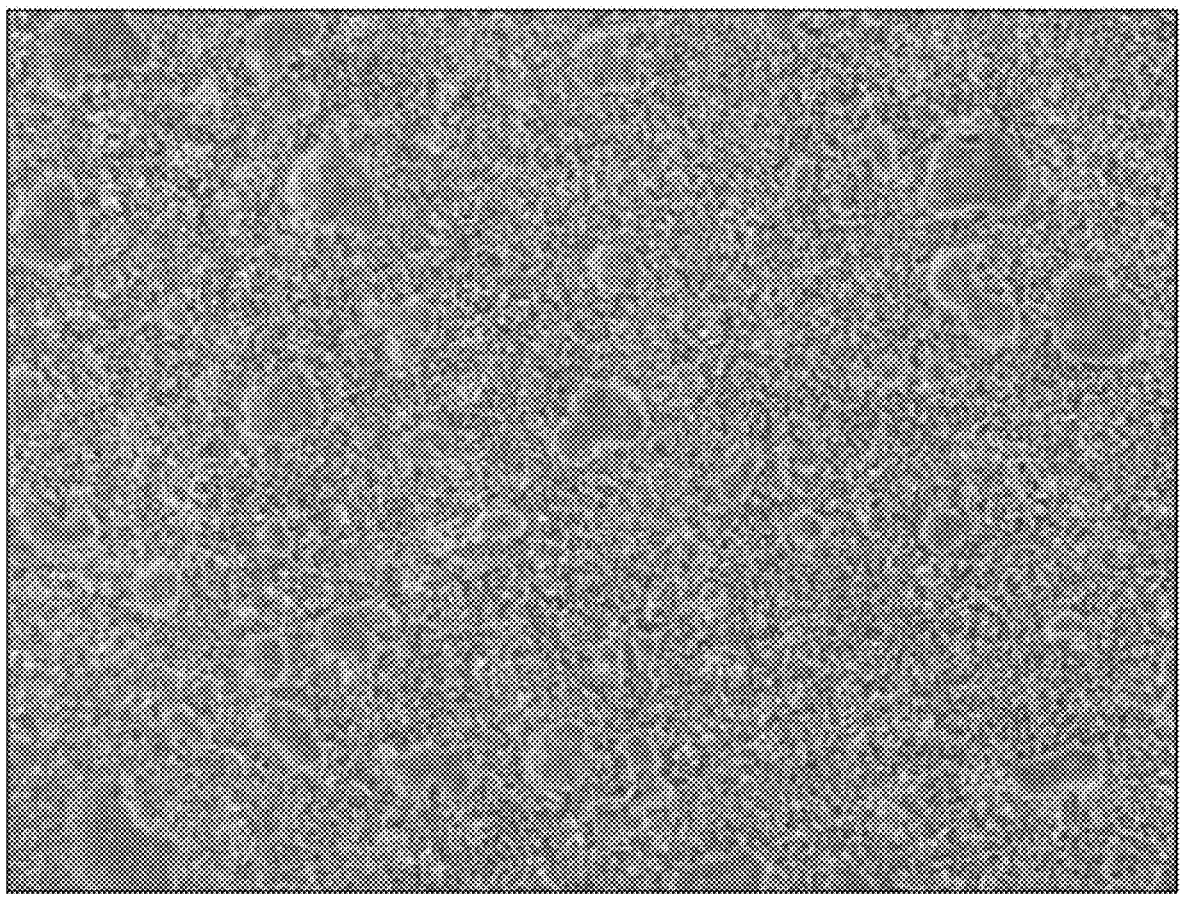
FIGS. 10a and 10b images showing an optimal treatment concentration of ECM according to an embodiment of the present disclosure (derived from embryonic stem cells)
Figure 10B:
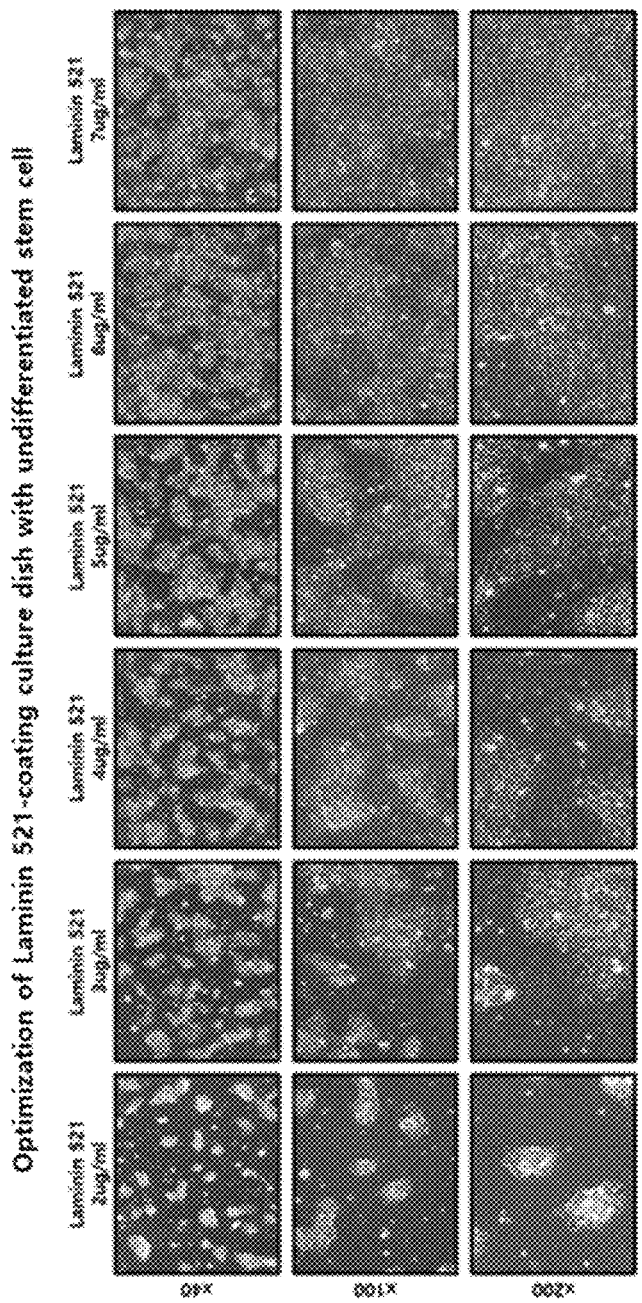

The results are shown in FIGS. 10a and 10b. In CELL-start, no problems happened until the steps of culturing stem cells and maintaining neural rosettes. However, the cells barely remained attached, but were floated or grew in a mesh pattern in the step of differentiating into dopaminergic precursor cells and proliferating the same (FIG. 10a). At Laminin-521 concentrations of 2 μg/mL and 3 μg/mL, the cells exhibited too poor adhesion to conduct the test. When Laminin-21 was used at concentrations of 6 μg/mL and 7 μg/mL, the cells underwent spontaneous differentiation at high frequency. In contrast, the Laminin-521 concentrations of 4 μg/mL and 5 μg/mL guaranteed relatively high adhesion, with most preference for 5 μg/mL in terms of cell morphology and count under the same time condition (FIG. 10b).

Based on the results, it was most reasonable to employ CELLstart in the stem cell culturing step and Laminin-521 at the concentration of 5 μg/mL in all of the subsequent steps except for the embryoid body step.

Experimental Example 7: Mass Proliferation of Dopaminergic Neural Precursor Cells (Increase in Differentiation Rate)

As a rule, mass production in a GMP facility takes separate protocols for MCB (Master Cell Bank) obtained by proliferating and storing a large amount of undifferentiated stem cells and for WCB (Working Cell Bank) obtained by proliferating and storing a large amount of dopaminergic neural precursor cells for transplantation. Therefore, the time points of preparing WCB from MCB and thawing WCB to proliferate dopaminergic precursor cells in a large amount are very important in increasing the differentiation rate while decreasing cell proliferation rates to some degree to guarantee stability against proliferation upon transplantation.

Figure 11A:
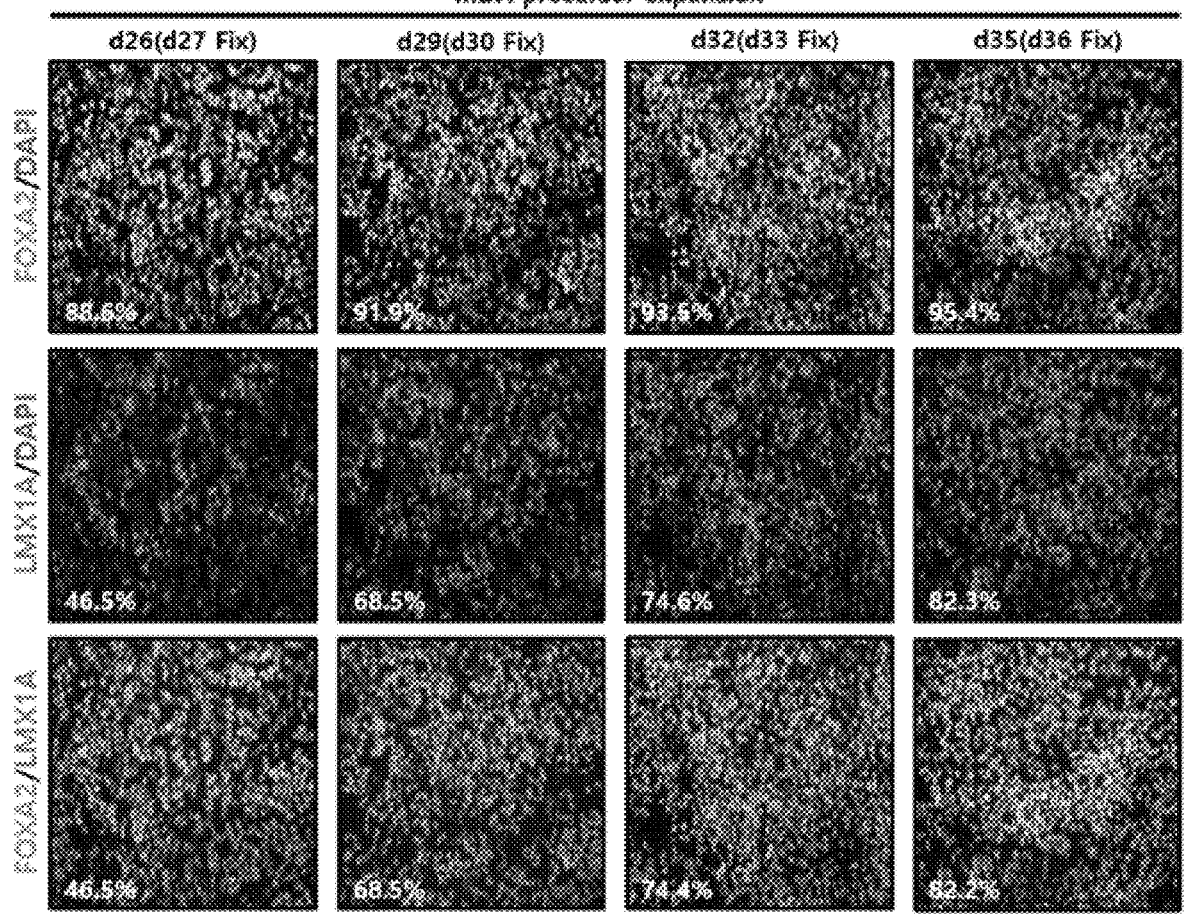
FIGS. 11a and 11b are images showing the final differentiation rate of dopaminergic neural precursor cells according to an embodiment of the present disclosure (11a: derived from embryonic stem cells, 11b: derived from induced pluripotent stem cells)
Figure 11B:
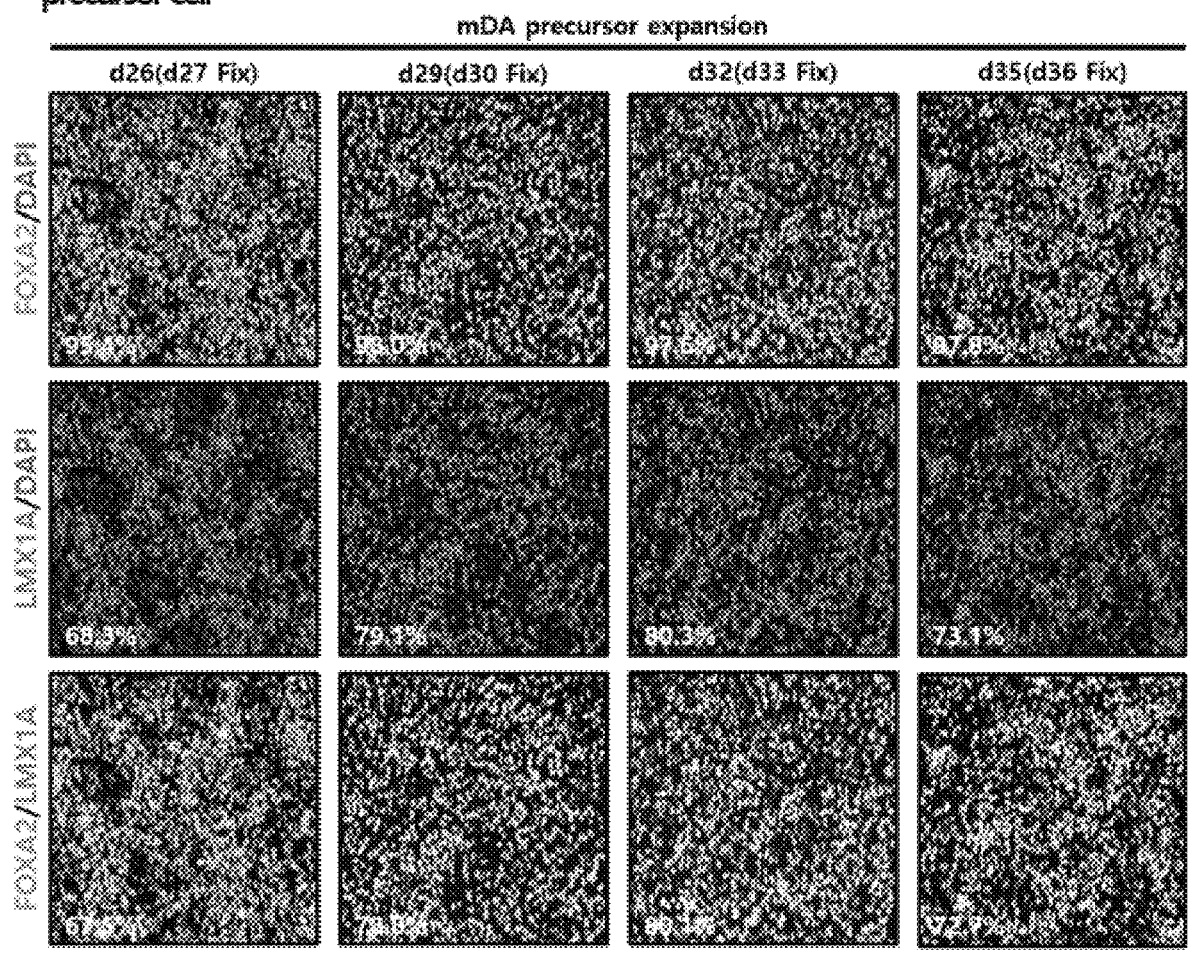

In this regard, stem cells were differentiated into dopaminergic precursor cells by using the protocols of the above Examples while monitoring expression levels of FOXA2 and/or LMX1A. As shown in FIGS. 11a and 11b, expression levels of FOXA2 and/or LMX1A were measured to increasingly increase from differentiation day 27 to day 36. Meanwhile, when differentiation was conducted beyond day 35, the differentiation rate was rather decreased and the cell morphology increasingly escaped from the morphological scope of the precursors (the same morphology as that upon ceasing treatment with SAG and CHIR99021 on differentiation day 35 in FIG. 8c). For this reason, the cells on differentiation day 35 were determined to undergo the final differentiation.

Accordingly, differentiation day 26 was set forth as the time point of preparing NCB in the present disclosure (because the same differentiation rate must be measured between the method in which cells are not frozen, but are differentiated in a continuous manner and the method in which cells are frozen and thawed before differentiation, based on the result of Experimental Example 4-1). Selection was made of the cells on day 35 obtained by thawing WCB on day 26 and proliferating the same for 9 days.

Figure 12:
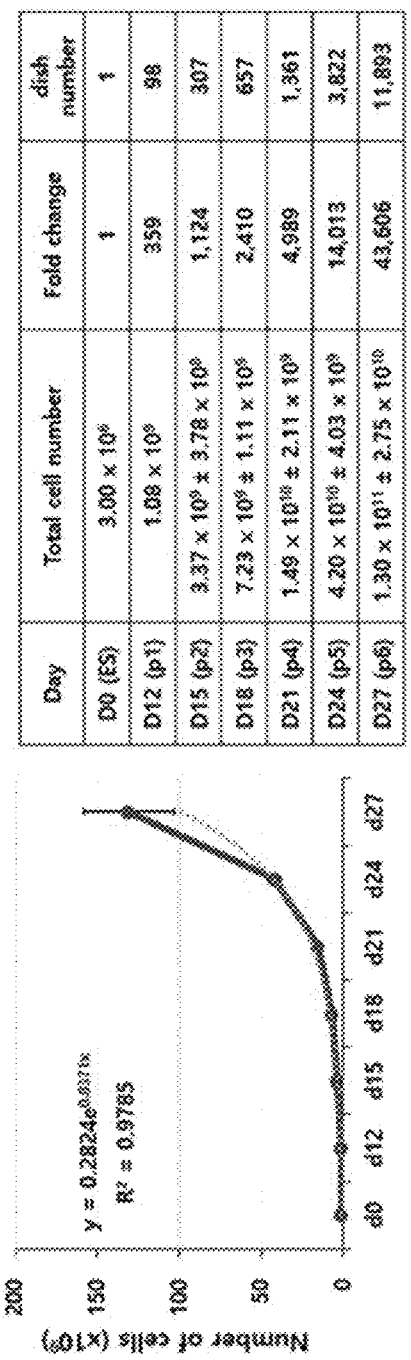
FIG. 12 shows a graph, together with a table, indicating the mass production of dopaminergic neural precursor cells according to an embodiment of the present disclosure (derived from embryonic stem cells)

Therefore, as can be seen in FIG. 12, the protocol of the present disclosure can produce about 130 billion dopaminergic neural precursor cells from one vial (about $3 \times 10^6$ cells) of MCB (Master Cell Bank) through differentiation.

Experimental Example 8: In Vivo Transplantation of Cells Prepared Using the Inventive Protocol 8-1. Construction of 6-OHDA Injured Parkinson's Disease (PD)-Model Female Sprague-Dawley lineage rats (Orient Bio Inc.), each weighing 200-250 g, were used as subjects. They were anesthetized with a mixture of 30 mg/kg Zoletil (Virbac) and 10 mg/kg Rompun (Bayer). According to the coordinates (AP −0.40, ML −0.13, DV −0.70, TB −0.45), 3 μL of 30 mM 6-OHDA was injected into the medial forebrain bundle of each rat to create a hemi-parkinsonian model.

8-2. Behavioral Recovery of PD-Nod after Transplantation of Cells Prepared Using Inventive Protocol Stem cells were differentiated according to the differentiation protocols of the above Examples. The differentiated cells on differentiation day 35 (d35) were suspended at the final concentration of $8.75 \times 10^4$ cell/μL in PBS (CTS) to prepare a cml suspension for transplantation. For a control, a group transplanted with PBS alone was used. Four weeks after 6-OHDA injury in Experimental Example 8-1, the animals were divided into groups and then subjected to immunosuppression by intraperitoneally injecting cyclosporine A (Chong Kun Dang Pharmaceutical Corp) at a daily dose of 10 mg/kg thereto. The cell suspension thus obtained was transplanted in an amount of 4 μL into each rat in a stereotactic manner according to the coordinates (AP+ 0.08, ML −0.30, DV −0.40 and −0.50, TB −0.24). Before transplantation, or 4, 8, 12, or 16 weeks after transplantation, amphetamine (2.5 mg/kg, Sigma-Aldrich) was intraperitoneally injected, followed by monitoring whether the rats rotated within 30 min following injection. For comparison, the same experiment was carried out with dopaminergic neural precursor cells derived from H9 human embryonic stem cells (H9 hESCs, WiCell Inc., U. S. A).

Figure 13A:
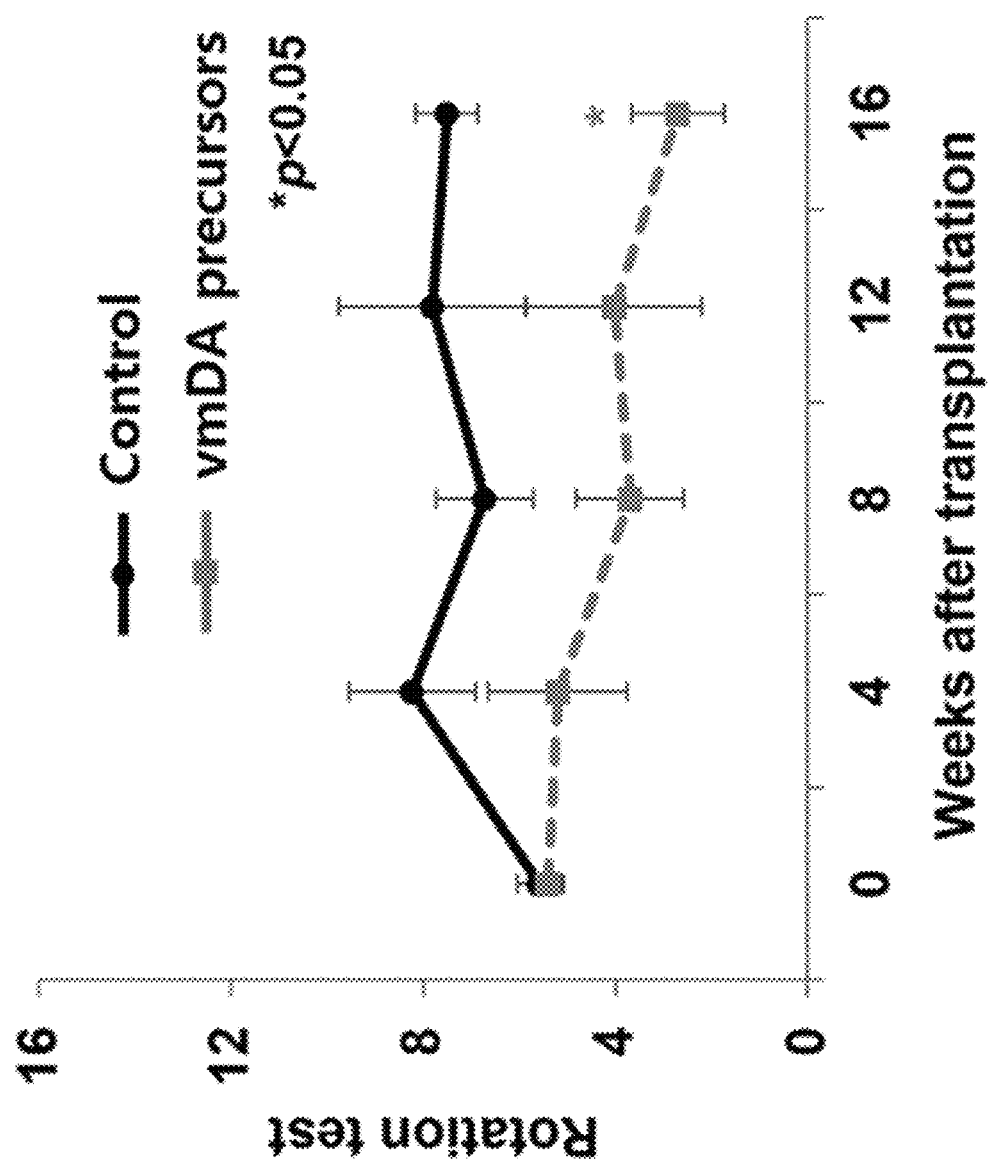
FIGS. 13a and 13b are plots showing in vivo efficacy of dopaminergic neural precursor cells according to an embodiment of the present disclosure (derived from embryonic stem cells).
Figure 13B:
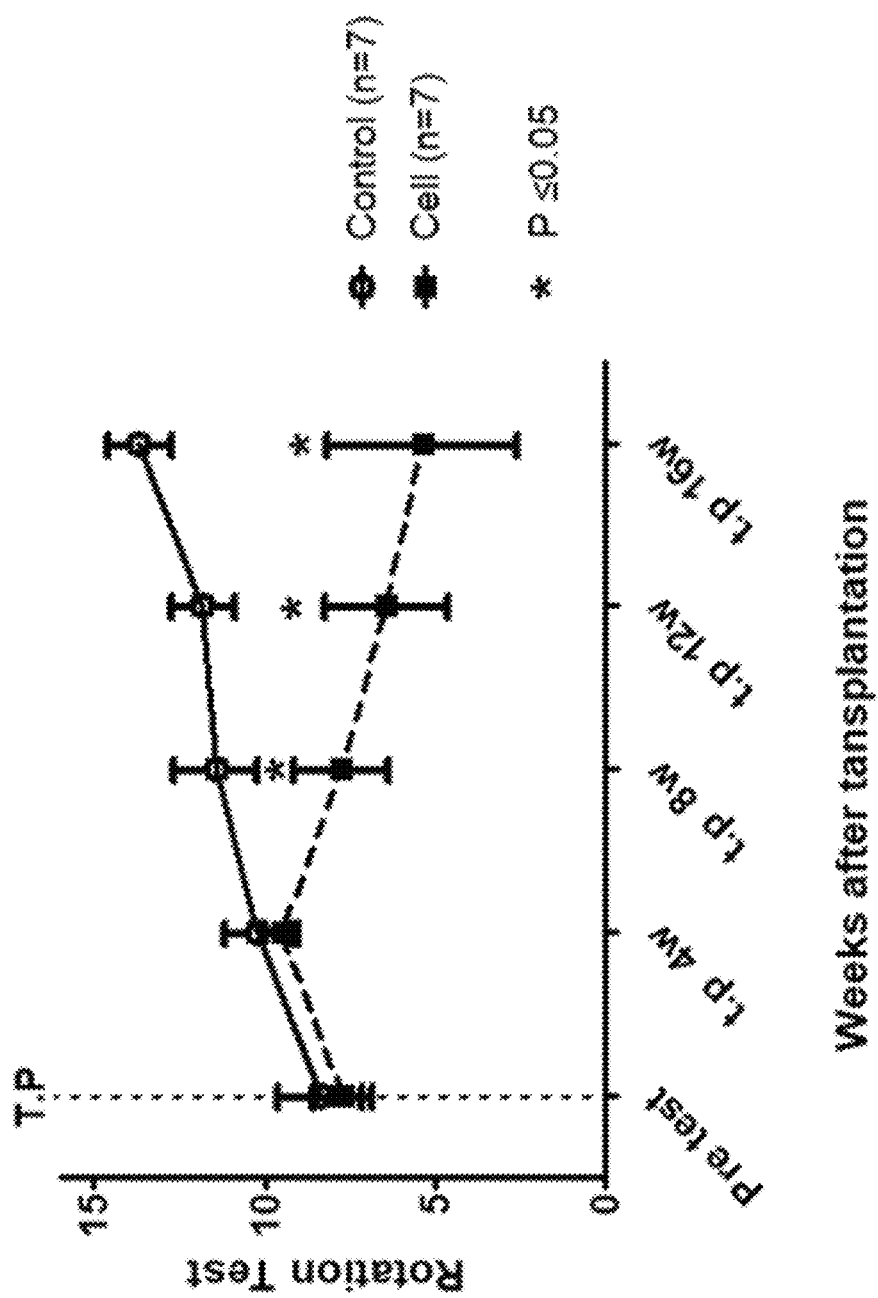

Compared to the control, as shown in FIGS. 13a and 13b, the rats into which the cells differentiated by the conventional method (the H9 embryonic stem el-derived dopaminergic neural precursor cells) were transplanted were observed to improve in motor function significantly only 16 weeks after transplantation (FIG. 13a) whereas the rats transplanted with the cells differentiated according to the method (protocol) of the present disclosure were observed to improve in motor function significantly all 8, 12, and 16 weeks after transplantation (FIG. 13b).

These results imply that the cells prepared according to the method (protocol) of the present disclosure can survive in vivo at higher efficiency and have a greater effect of improving motor functions.

INDUSTRIAL APPLICABILITY

The present invention relates to a method for inducing differentiation of stem cells into midbrain-specific dopaminergic neural precursor cells and for mass production of stem ell-derived midbrain-specific dopaminergic neural precursor cells.

As described hitherto, the present disclosure pertains to a method for inducing the differentiation of stem cells into dopaminergic neural precursor cells and a method for mass production of dopaminergic neural precursor cells. Having ability to effectively differentiate stem cells into neural precursor cells, the methods of the present disclosure can find advantageous applications in research and development and commercialization associated therewith.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for inducing differentiation of stem cells into dopaminergic neural precursor cells, the method comprising the steps of:
   a) culturing stem cells in a monolayer format by adding a BMP signaling inhibitor and an activin/nodal signaling inhibitor;
   b) forming and maintaining an embryoid body by adding a BMP signaling inhibitor, an activin/nodal signaling inhibitor, a sonic hedgehog (SHH) signaling activator, and a GSK-3 inhibitor (Wnt signaling activator);
   c) generating a neural rosette; and
   d) differentiating the neural rosette into dopaminergic neural precursor cells,
   wherein step b) is carried out by adding the BMP signaling inhibitor and the activin/nodal signaling inhibitor daily from the starting day of the step and adding the SHH signaling activator and GSK-3 inhibitor (Wnt signaling activator) daily from days 2-6 after the starting day of the step.

2. The method of claim 1, further comprising a step of:
   e) proliferating the dopaminergic neural precursor cells through passage.

3. The method of claim 1, wherein the stem cells are embryonic stem cells, induced pluripotent stem cells (iPSCs), adult stem cells, somatic cell nuclear transfer embryonic stem cells, or stem cells formed by direct reprogramming.

4. The method of claim 1, wherein the stem cells are cultured in a medium containing an extracellular matrix (ECM).

5. The method of claim 1, wherein step a) is carried out by daily adding the BMP signaling inhibitor and the activin/nodal signaling inhibitor from 1-3 days before the end of the step.

6. The method of claim 1, wherein step c) is carried out by adding an SHH signaling activator and a GSK-3 inhibitor (Wnt signaling activator) daily from the starting day of the step.

7. The method of claim 1, wherein step d) is carried out by adding an SHH signaling activator and a GSK-3 inhibitor (Wnt signaling activator) daily from the starting day of the step.

8. The method of claim 1, wherein step d) is carried out by exchanging the medium with a fresh medium every day and passaging the cells every three days.

9. The method of claim 5, wherein the BMP signaling inhibitor is dorsomorphin and the activin/nodal signaling inhibitor is 4-(5-benzo[1,3]dioxol-5-yl-4-pyridin-2-yl-1H-imidazol-2-yl)-benzimide (SB431542).

10. The method of claim 1, wherein the SHH signaling activator is SAG (smoothened agonist) and the GSK-3 inhibitor (Wnt signaling activator) is CHIR99021.

11. The method of claim 1, wherein the method has a rate of differentiation into dopaminergic neural precursor cells of 80% or higher.

12. The method of claim 1, wherein dopaminergic neural precursor cells have increased expression levels of FOXA2 and/or LMX1A.

13. The method of claim 1, wherein the dopaminergic neural precursor cells alleviate symptoms of Parkinson's disease.

14. A method for mass production of dopaminergic neural precursor cells, the method comprising the steps of:

a) culturing stem cells in a monolayer format by adding a BMP signaling inhibitor and an activin/nodal signaling inhibitor;
b) forming and maintaining an embryoid body by adding a BMP signaling inhibitor, an activin/nodal signaling inhibitor, a sonic hedgehog (SHH) signaling activator, and a GSK-3 inhibitor (Wnt signaling activator);
c) generating a neural rosette;
d) differentiating the neural rosette into dopaminergic neural precursor cells; and
e) proliferating the dopaminergic neural precursor cells through passage, wherein step b) is carried out by adding the BMP signaling inhibitor and the activin/nodal signaling inhibitor daily from the starting day of the step and adding the SHH signaling activator and GSK-3 inhibitor (Wnt signaling activator) daily from days 2-6 after the starting day of the step.

* * * * *